US006572874B1

(12) United States Patent
Harrison et al.

(10) Patent No.: US 6,572,874 B1
(45) Date of Patent: Jun. 3, 2003

(54) VAGINAL DELIVERY OF BISPHOSPHONATES

(75) Inventors: Donald C. Harrison, Cincinnati, OH (US); James H. Liu, Cincinnati, OH (US); Giovanni M. Pauletti, Loveland, OH (US); Wolfgang A. Ritschel, Cincinnati, OH (US)

(73) Assignee: UMD, Inc., Cincinnati, OH (US)

( * ) Notice: Subject to any disclaimer, the term of this patent is extended or adjusted under 35 U.S.C. 154(b) by 0 days.

(21) Appl. No.: 09/626,025

(22) Filed: Jul. 27, 2000

Related U.S. Application Data

(63) Continuation-in-part of application No. 09/079,897, filed on May 15, 1998, now Pat. No. 6,197,327.
(60) Provisional application No. 60/146,218, filed on Jul. 28, 1999.

(51) Int. Cl.[7] .......................... A61F 6/06; A61F 13/02; A61F 6/14; A61F 13/00
(52) U.S. Cl. ...................... 424/430; 424/431; 424/433
(58) Field of Search ................. 424/433, 431, 424/430

(56) References Cited

U.S. PATENT DOCUMENTS

| | | | |
|---|---|---|---|
| 3,852,155 A | 12/1974 | Moore | 195/1.8 |
| 4,016,270 A | 4/1977 | Pharriss et al. | 424/242 |
| 4,073,743 A | 2/1978 | Midler, Jr. et al. | 252/309 |
| 4,250,166 A | 2/1981 | Maekawa et al. | 424/81 |
| 4,318,405 A | 3/1982 | Sneider | 128/263 |
| 4,405,323 A | 9/1983 | Auerbach | 604/285 |
| 4,560,549 A | 12/1985 | Ritchey | 424/18 |
| 4,615,697 A | 10/1986 | Robinson | 604/890 |
| 4,698,359 A | * 10/1987 | Niederer et al. | 424/DIG. 15 |
| 4,789,667 A | 12/1988 | Makino et al. | 514/161 |
| 4,863,725 A | 9/1989 | Deckner et al. | 424/81 |
| 4,973,468 A | * 11/1990 | Chiang et al. | 424/447 |

(List continued on next page.)

FOREIGN PATENT DOCUMENTS

| | | | |
|---|---|---|---|
| WO | WO 87/02576 | 5/1987 | A61F/5/46 |
| WO | WO 89/03207 | 4/1989 | A61K/9/50 |
| WO | WO-98/01159 | * 1/1998 | |
| WO | WO 98/01159 | * 1/1998 | |
| WO | WO-98/56323 | * 12/1998 | |

OTHER PUBLICATIONS

Hamdy Role of bisphosphonates in metabolic bone diseases Trends in Endocrinol Metab 4:19–25 1993.*
C. P. Peter, DVM, PhD., et al., Comparative Study of Potential for Bisphosphonates to Damage Gastric Mucosa of Rats, *Digestive Diseases and Sciences*, vol. 43/5:1009–1015 (May 1998).
Lene Mortensen, et al., Risedronate Increases Bone Mass in an Early Postmenopausal Population: Two Years of Treatment Plus One Year of Follow–Up, Journal of *Clinical Endocrinology and Metabolism*, vol. 83/2:396–401.
Paul D. Miller, MD, A Randomized, Double–blind Comparison of Risedronate and Etidronate in the Treatment of Paget's Disease of Bone, *The American Journal of Medicine*, vol. 106:513–520 (May 1999).
C. P. Peter, DVM, PhD, et al., Esophageal Irritation due to Alendronate Sodium Tablets, *Digestive Diseases and Sciences*, vol. 43/9:1998–2002 (Sep. 1998).

(List continued on next page.)

*Primary Examiner*—Thurman K. Page
*Assistant Examiner*—Todd D Ware
(74) *Attorney, Agent, or Firm*—Hana Verny

(57) ABSTRACT

Devices, methods, and compositions for vaginal delivery of bisphosphonates. A targeted site delivery of bisphosphonates to the vagina using a medicated intravaginal device comprising a bisphosphonate composition formulated for transvaginal delivery. A method for treatment of osteoporosis and related bone and skeleton diseases, for prevention of bone breakdown and loss of bone mass and strength by intravaginal administration of bisphosphonates to the vagina and transvaginal delivery of bisphosphonates to the general circulation.

27 Claims, 5 Drawing Sheets

U.S. PATENT DOCUMENTS

| | | | |
|---|---|---|---|
| 4,983,392 A | 1/1991 | Robinson | 424/427 |
| 5,026,543 A | 6/1991 | Rijke | 424/81 |
| 5,084,277 A | 1/1992 | Greco et al. | 424/433 |
| 5,185,146 A | 2/1993 | Altenburger | 424/89 |
| 5,192,802 A | 3/1993 | Rencher | 514/535 |
| 5,201,326 A | 4/1993 | Kubicki et al. | 128/832 |
| 5,246,697 A | 9/1993 | Conte et al. | 424/78.03 |
| 5,273,521 A | 12/1993 | Peiler et al. | 604/13 |
| 5,275,820 A | 1/1994 | Chang | 424/426 |
| 5,314,915 A | 5/1994 | Rencher | 514/535 |
| 5,330,761 A | 7/1994 | Baichwal | 424/469 |
| 5,362,498 A | 11/1994 | Aiache | 424/435 |
| 5,393,528 A | 2/1995 | Staab | 424/436 |
| 5,472,704 A * | 12/1995 | Santus et al. | 424/435 |
| 5,527,534 A | 6/1996 | Myhling | 424/430 |
| 5,540,581 A | 7/1996 | Aida et al. | 514/415 |
| 5,788,980 A | 8/1998 | Nabahi | 424/430 |
| 5,912,006 A * | 6/1999 | Bockow et al. | 424/430 |

OTHER PUBLICATIONS

Gregory R. Mundy, M.D., et al., Bisophosphonates as Anticancer Drugs, *The New England Journal of Medicine*:398–400 (Aug. 6, 1998).

Henry G. Bone, et al., Dose–Response Relationships for Alendronate Treatment in Osteoporotic Elderly Women, *Journal of Clinical Endocrinology and Metabolism*, vol. 82/1:265–274.

Sohail A. Khan, et al., Elimination and Biochemical Responses to Intravenous Alendronate in Postmenopausal Osteoporosis, *Journal of Bone and Mineral Research*, vol. 12/10:1700–1707 (1997).

Christian Roux et al., Treatment of Patients with Paget's Disease of Bone, *Drugs*, vol. 58/5:823–830 (Nov. 1999).

Lisa Brannon–Peppas, Novel Vaginal Drug Release Applications, *Advanced Drug Delivery Reviews*,:169–177 (1993).

Ingo J. Diel, Antitumour Effects of Bisphosphonates, First Evidence and Possible Mechanisms, *Drugs*, vol. 59/3:391–399 (Mar. 2000).

Kenneth G. Saag, M.D., et al., Alendronate for the Prevention and Treatment of Glucocorticoid–Induced Osteoporosis, *The New England Journal of Medicine*, vol. 339/5:292–299 (Jul. 30, 1998).

Steven T. Harris, MD., et al., Effects of Risedronate Treatment on Vertebral and Nonvertebral Fractures in Women With Postmenopausal Osteoprosis, A Randomized Controlled Trial, JAMA, vol. 282/14:1344–1352 (Oct. 13, 1999).

Clifford J. Rosen, et al., Comparative Clinical Pharmacology and Therapeutic Use of Bisphosphonates in Metabolic Bone Diseases, *Drugs*, vol. 51/4:537–555 (Apr. 1996).

W. A. Ritschel, et al., Pharmacokinetics of PFA (Trisodium Phosphonoformate) after I.V. and P.O. Administration to Beagle Dogs and Rabbits, *Meth and Find Exptl Clin Pharmacol*, vol. 7/1:41–48 (1985).

P. Mura, et al., Evaluation of Transcutol as a Clonazepam Transdermal Permeation Enhancer from Hydrophilic Gel Formulations, *European Journal of Pharmaceutical Sciences, European Journal of Pharmacetical Sciences*, vol. 9:365–372 (2000).

A. S. Hussain, et al., "Body Burden" of Phosphonoformic Acid After Topical and Vaginal Administration to Rabbits and Beagle Dogs, vol. 11/2:111–114 (1989).

Wendy Jeal, et al., Alendronate, A Review of its Pharmacological Properties and Therapeutic Efficacy in Postmenopausal Osteoporosis, *Drugs*, vol. 53/3:415–434 (Mar. 1997).

Matthew R. Smith, MD, PhD, Bisphosphonates as Anticancer Agents, Premiere Issue:6–7 (1999).

* cited by examiner

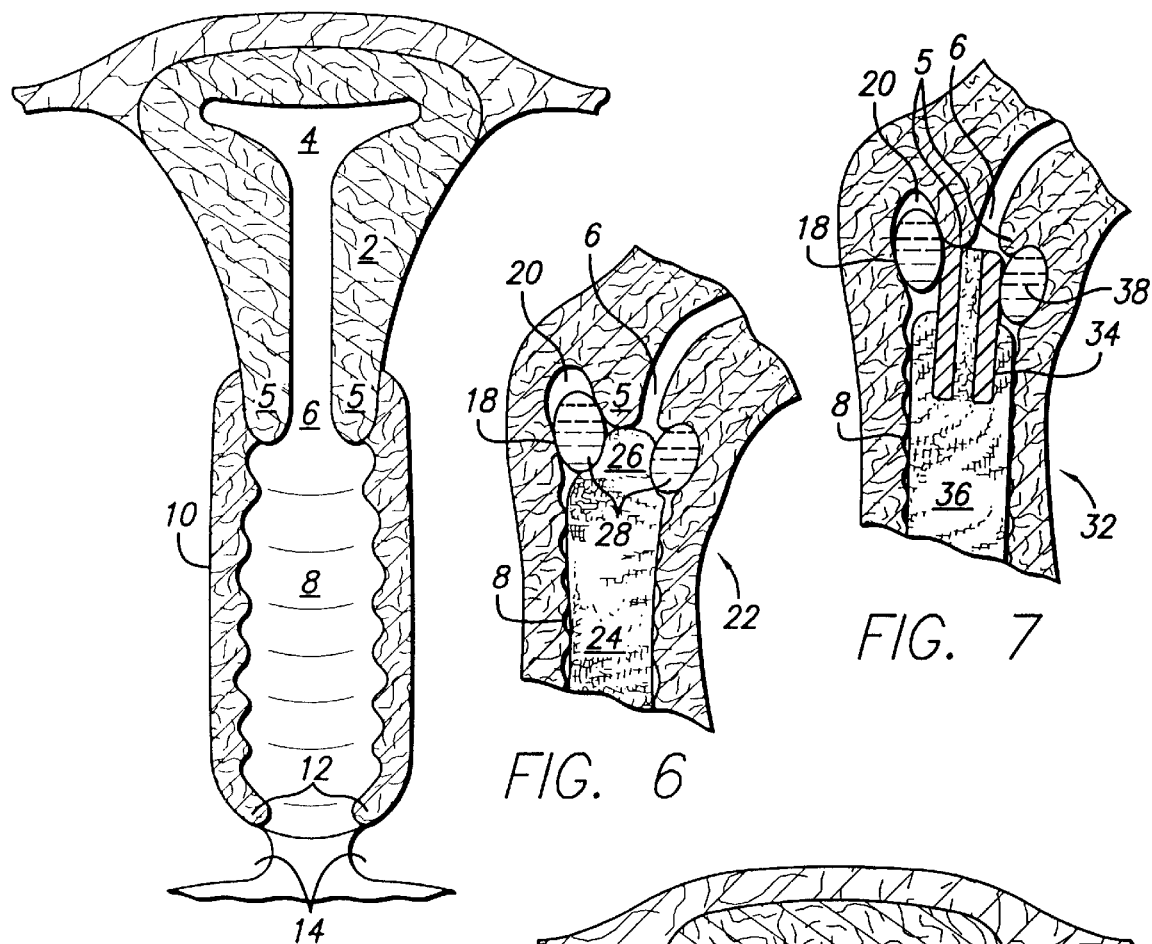
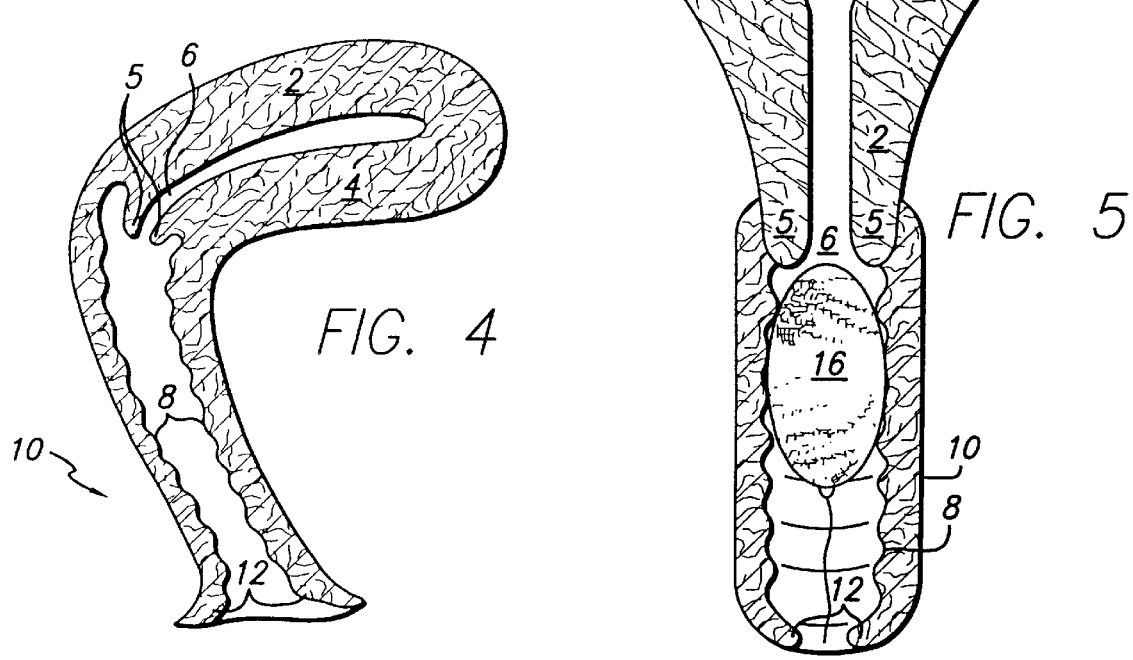
FIG. 3
FIG. 4
FIG. 5
FIG. 6
FIG. 7

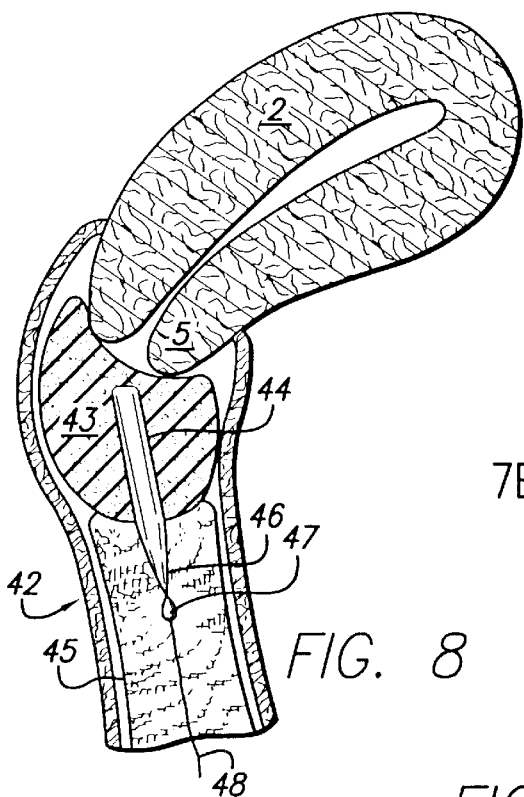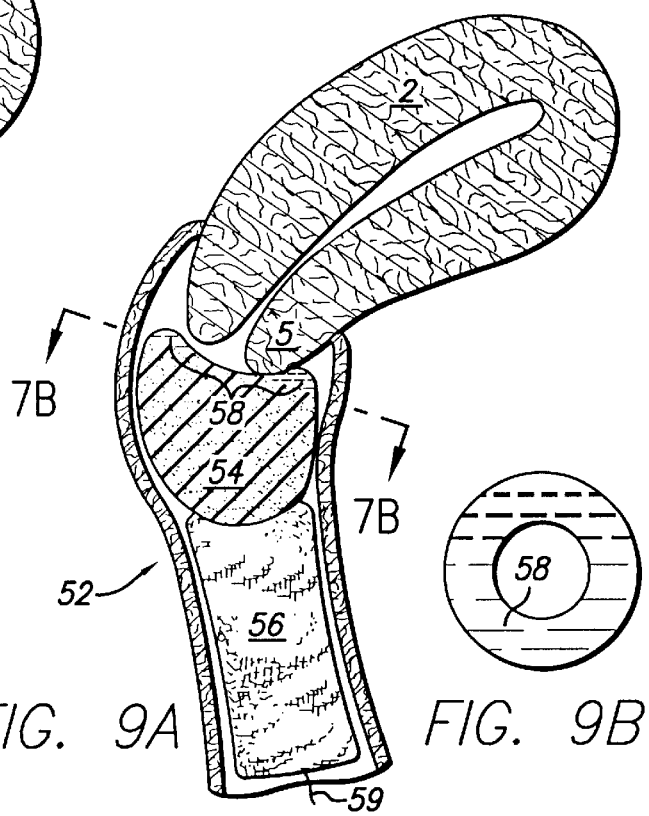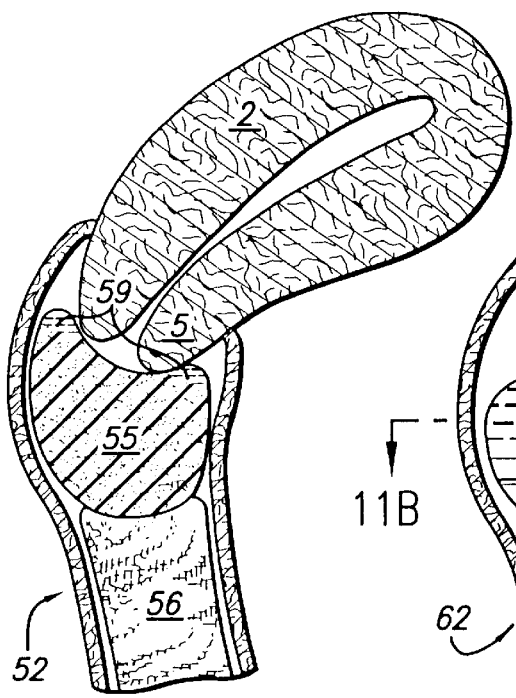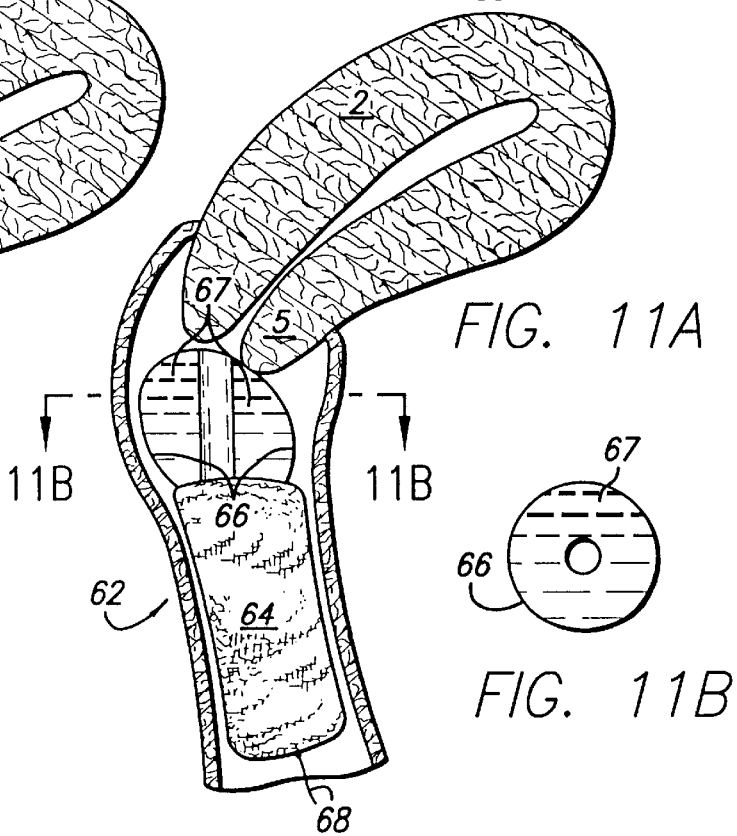
FIG. 8
FIG. 9A  FIG. 9B
FIG. 10
FIG. 11A  FIG. 11B

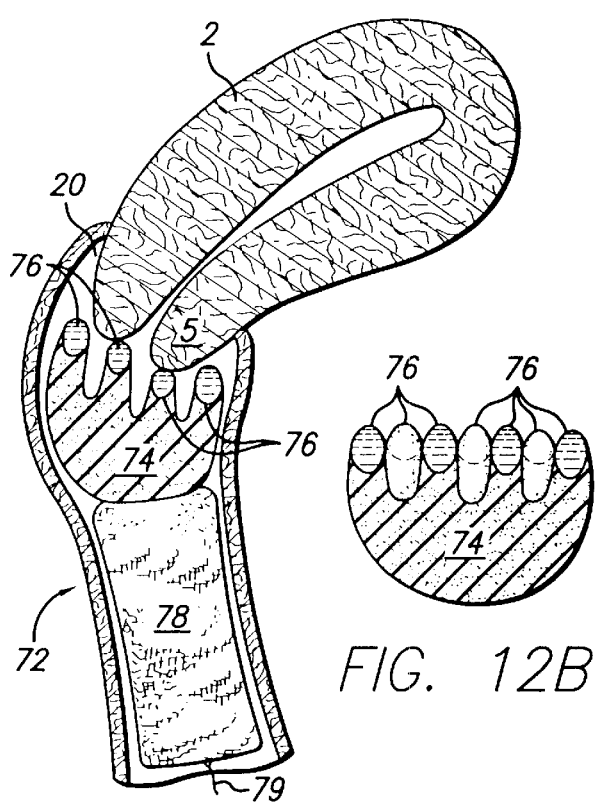
FIG. 12A
FIG. 12B
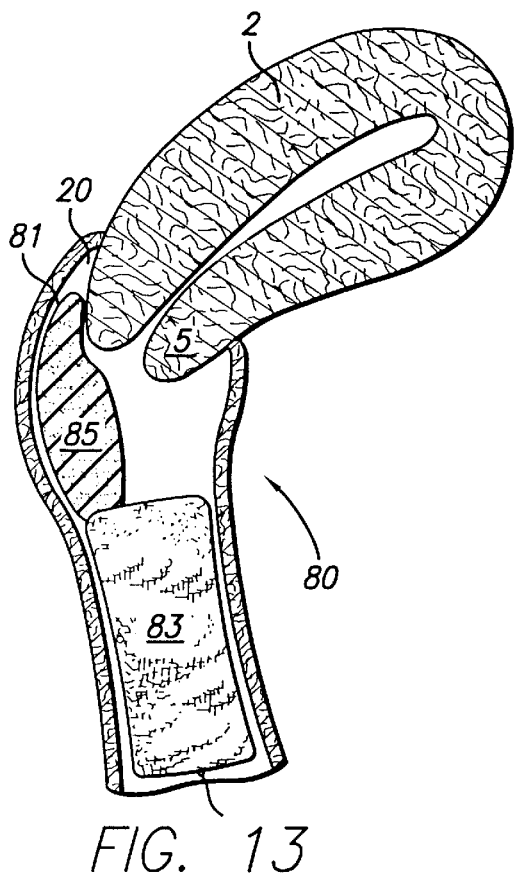
FIG. 13
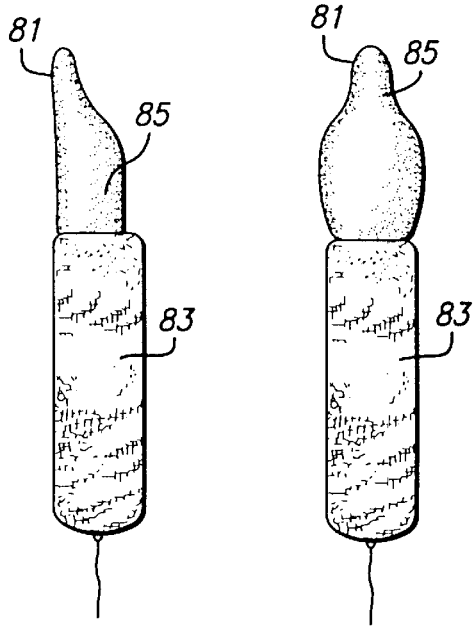
FIG. 14  FIG. 15
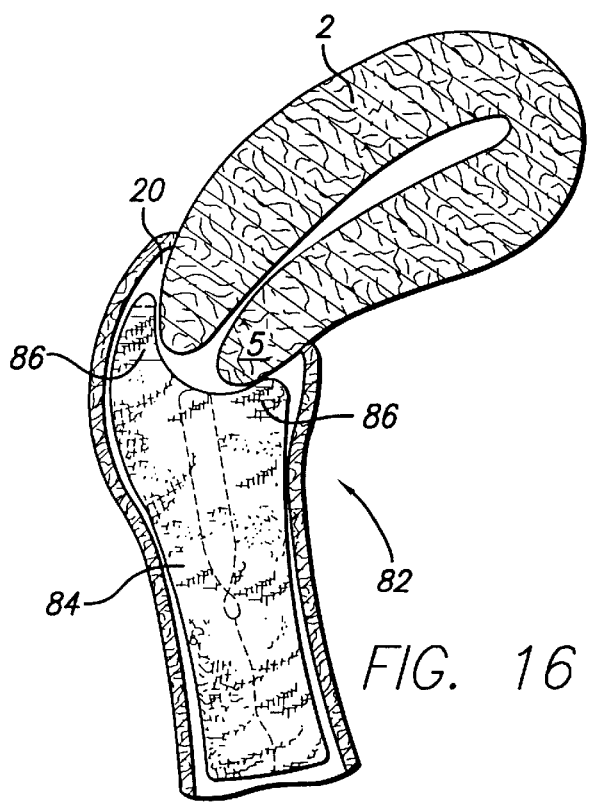
FIG. 16

VAGINAL DELIVERY OF BISPHOSPHONATES

This application is a continuation-in-part of 09/079,897 filed on May 15, 1998, now U.S. Pat. No. 6,197,327 and is also partially based on and claims priority of the Provisional Application Ser. No. 60/146,218 filed on Jul. 28, 1999.

BACKGROUND OF THE INVENTION

1. Field of the Invention

The present invention concerns devices, methods, compositions and formulations for vaginal delivery of a class of drugs in the bisphosphonate group. In particular, the invention concerns a targeted site delivery of bisphosphonates to the vagina using a bisphosphonate comprising vaginal composition or a medicated intravaginal device comprising the bisphosphonate composition formulated for transvaginal delivery. The composition or the device of the invention delivers 10 to 30 times more bisphosphonates intravaginally as can be delivered orally due to the absorption of bisphosphonates from the vagina which far exceeds the absorption of bisphosphonates from the gastrointestinal tract. Vaginal administration generally avoids major problems connected with oral administration, such as gastric and esophageal reflux and ulceration.

The invention also concerns a method for treatment of osteoporosis, Paget's disease, metastatic cancer of bone, and other related diseases of bone and skeleton and for prevention of bone breakdown and loss of bone mass and strength by intravaginal administration of bisphosphonates via the vagina and by transvaginal delivery of bisphosphonates to general circulation. This novel and unique route of administration provides a mechanism for delivering drugs to prevent and treat osteoporosis in a way now only available with considerable side effects.

2. Background and Related Art

Osteoporosis and therewith associated loss of bone mass and strength leading to bone breakdown and fractures is a major medical problem in postmenopausal women.

It is estimated that eight million women in the United States have osteoporosis and that an additional 15.4 million women have low bone mass, placing them at increased risk for development of osteoporosis. These risks are most profound after menopause when the rate of bone loss is accelerated. Osteoporosis leads to fractures in the spine and hips in a significant number of these women, markedly altering their lifestyle and reducing their life expectancy.

In the past decade, hormone replacement therapy with estrogens has been the mainstay in the treatment of postmenopausal women. Recent studies, however, have shown that this treatment is not suitable for all female patients and that it possesses an increasing risk of certain female cancers and the heightened malignancy of cancers once they occur. For that reason, alternate therapies for osteoporosis have been and are continually sought.

A number of approaches for prevention of osteoporosis in this patient group have been proposed. These approaches include the administration of high doses of calcium and vitamin D in conjunction with the administration of estrogens, and the administration of synthetic substances which bind to estrogen receptors such as raloxifen, tamoxifen, etc.

One of the new approaches which has been suggested and investigated is the administration of bisphosphonates. Bisphosphonates prevent the resorption of bone, thereby reducing occurrences of fractures, especially of the spine and hip. Recent studies have demonstrated these compounds act to prevent the loss of bone and to enhance bone density in the postmenopausal female population and in patients with Paget's disease of bone (*Journal of Clinical Endocrinology and Metabolism*, 82(1):265–274 (1997); *Journal of Bone and Mineral Research*. 12(10):1700–1707 (1997); *American Journal of Medicine*, 106(5):513–520 (1997); *Journal of Clinical Endocrinology and Metabolism*. 83(2):396–402 (1998)).

As described in the above references, bisphosphonates have recently been shown to prevent the continuous breakdown of bone in the vulnerable population and lead to strengthening of bone and an increase in bone mass. In several studies, these compounds have been shown to markedly reduce fractures.

In addition to treating osteoporosis and Paget's disease, the clinical use of bisphosphonates for cancer has increased dramatically in recent years. *New England Journal of Medicine*, 335:1785–1791 (1996) reports that treatment with bisphosphonates decreases the frequency of skeletal events for patients with multiple myeloma involving bone and breast cancer with osteolytic metastases. Recent clinical trials have shown that adjunctive treatment with bisphosphonates reduces the incidence and number of new bone and visceral metastases in women with high risk, primary breast cancer (*New England Journal of Medicine*. 339:398–400 (1998)).

There are at least ten bisphosphonates now available for therapy worldwide, but major problems with their administration have been noted.

The main problems with oral administration of bisphosphonates relate to absorption and gastrointestinal tolerability. Absorption is poor and drug administration recommendations must be given to the patient and checked. Etidronate, tiludronate and risedronate need to be taken two hours before or after a meal with a large volume of water, and dairy products or antacids are forbidden within two hours of administration. Alendronate has been given in the early morning, immediately upon rising, while in the upright position, two hours before any food or drink. Upper gastrointestinal adverse effects are reported in 15–20% of patients with orally administered bisphosphonates. Esophagitis has been reported in a small number of patients with osteoporosis treated with 10 mg/day alendronate. (*Drugs*, 58:827 (1999)).

Generally, thus, the bisphosphonates oral administration requires a strict regimen. In most patients, this regimen has proven to be inconvenient and impractical leading to a failure of oral administration.

In addition, a significant number of women taking these compounds develop irritation of esophageal mucosa, esophageal reflux and esophagitis (*Digestive Diseases and Sciences*, 43(9):1998–2002 (1998); *Digestive Diseases and Sciences*, 43(5):1009–1015 (1998)).

Even if these inconveniences and complications could be overcome, to deliver a sufficient amount of bisphosphonates is also problematic because only less than 1% of the bisphosphonates are generally absorbed following oral administration (*Drugs*, 53(3):415–434 (1997). For these reasons, as many as 35% all patients discontinue the oral treatment with bisphosphonates in one year.

Thus, it would be very important to provide an alternative composition and/or drug delivery route which would avoid problems associated with bisphosphonate oral administration and still provide a patient with a therapeutically effective amount of bisphosphonates.

The major difficulties encountered with the administration of bisphosphonate compounds are their poor absorption from the gastrointestinal tract, their interaction with other drugs and foods which alters their absorption, and their tendency to damage mucosa and irritate the esophagus and stomach.

In view of the problems encountered with oral administration of bisphosphonates which limits their utility, it is clear that new delivery mechanisms which would enhance the absorption and bioavailability of these drugs, especially transvaginal administration with sustained-release administration would be extremely advantageous for achieving and increasing a therapeutic potential of bisphosphonates.

It is, therefore, an objective of the present invention to provide devices, methods and compositions for treating osteoporosis, Paget's disease and other related diseases of bone and skeleton or for treating and prevention of cancer by intravaginal delivery of effective doses of bisphosphonates to the vagina and by transvaginal transport of bisphosphonates into the general circulation after absorption of these drugs through a vaginal mucosa.

All references, patents and patent applications cited herein are hereby incorporated by reference in their entirety.

SUMMARY OF THE INVENTION

One aspect of the present invention is a device, a method, a composition, and a formulation for transvaginal delivery of bisphosphonates effective to treat osteoporosis, Paget's disease and other related diseases of bone and skeleton, into the general circulation.

Another aspect of this invention is a pharmaceutically acceptable composition for intravaginal delivery comprising a bisphosphonate selected from the group consisting of alendronate, clodronate, etidronate, pamidronate, tiludronate, ibandronate, zoledronate, olpadronate, residronate and neridronate formulated for effective transvaginal absorption for prevention and treatment of osteoporosis, Paget's disease, other diseases of bone and skeleton and cancer.

Still yet another aspect of this invention is a pharmaceutically acceptable composition comprising a bisphosphonate, selected from the group consisting of alendronate, clodronate, etidronate, pamidronate, tiludronate, ibandronate, zoledronate, olpadronate, residronate and neridronate, in dosage unit form, for intravaginal delivery to a human female for the purpose of treating or prevention of osteoporosis, Paget's disease, other diseases of bone and skeleton or cancer wherein said composition comprises a combination of an effective amount of the bisphosphonate with a nontoxic pharmaceutically acceptable excipient carrier, a mucoadhesive and/or penetration enhancing agent, wherein said composition is a vaginal suppository, tablet, bioadhesive tablet, capsule, microparticle, bioadhesive microparticle, cream, lotion, foam, ointment, solution, gel, or a sustained release gel, tablet or capsule, or a sustained release suppository administered directly to the vagina or incorporated into a device of the invention.

Still another aspect of this invention is a medicated intravaginal device, such as a medicated tampon, tampon-like device, pessary, ring, sponge, or cup comprising a bisphosphonate selected from the group consisting of alendronate, clodronate, etidronate, pamidronate, tiludronate, ibandronate, zoledronate, olpadronate, residronate and neridronate in a formulation suitable for intravaginal absorption and transvaginal delivery of the bisphosphonate agent to the general circulation.

Yet another aspect of this invention is a device for delivering intravaginally an effective amount of a bisphosphonate agent selected from the group consisting of alendronate, clodronate, etidronate, pamidronate, tiludronate, ibandronate, zoledronate, olpadronate, residronate and neridronate for treatment of osteoporosis, Paget's disease, metastatic cancer of bone, other bone or skeleton diseases or cancer and prevention of development of osteoporosis, wherein said device is a ring, strip, vaginal tampon, absorbent vaginal tampon, strip, capsule or suppository comprising tampon or tampon-like device.

Still yet another aspect of this invention is a method for treating a female patient suffering from, or being at risk of developing osteoporosis, Paget's disease, metastatic cancer to bone or other disease of bone or skeleton or cancer, said method comprising contacting the vaginal epithelium of the female patient with a composition comprising a therapeutically effective dose of bisphosphonate selected from the group consisting of alendronate, clodronate, etidronate, pamidronate, tiludronate, ibandronate, zoledronate, olpadronate, residronate and neridronate in admixture with a biocompatible pharmaceutically acceptable excipient for administration of the bisphosphonate to the vaginal epithelium, wherein said bisphosphonate is present in a pharmaceutical composition in an amount sufficient to attain, following intravaginal delivery of the composition and its absorption through the vaginal mucosa and transportation via venous and lymphatic channels to the circulation, a therapeutically effective amount of the bisphosphonate in the blood circulation of the patient.

Another aspect of this invention is a method for preparation of an intravaginal medicated device comprising incorporating a composition comprising a bisphosphonate agent selected from the group alendronate, clodronate, etidronate, pamidronate, tiludronate, ibandronate, zoledronate, olpadronate, residronate and neridronate with a device for intravaginal delivery of said agent, wherein said device is a vaginal tampon, a strip, capsule or container comprising tampon or a tampon-like device, vaginal strip, vaginal cup, vaginal ring, vaginal pessary, vaginal tablet, vaginal suppository, vaginal sponge, bioadhesive tablet, microparticle, or bioadhesive microparticle, and wherein said agent is formulated as a cream, lotion, foam, ointment, solution or gel.

BRIEF DESCRIPTION OF THE DRAWINGS

FIG. 3 is a cross-sectional representation of a portion of the female reproductive organs including the uterus and vagina in the upright orientation.

FIG. 4 is a cross-sectional side view representation of a portion of the female reproductive organs including the uterus and vagina.

FIG. 5 is the representation of FIG. 2 showing placement of a vaginal suppository for a drug delivery according to the present invention.

FIG. 6 is a cross-sectional side view representation of the vaginal area adjacent the cervix showing placement of a tampon drug delivery incorporating an annular delivery composition.

FIG. 7 is the representation of FIG. 3 showing placement of a tampon for drug delivery according to the present invention.

FIG. 8 is the representation of FIG. 3 showing placement of a tampon for drug delivery incorporating a distal porous foam section.

FIG. 9A is the representation of FIG. 4 showing placement of a tampon for drug delivery incorporating a distal porous foam cup. FIG. 9B is a cross-sectional view of the embodiment shown in FIG. 9A, taken in the direction indicated by the arrows labeled 9B in FIG. 9A.

FIG. 10 is an alternative embodiment to one shown in FIG. 8A in which medication is contained in the entire porous foam cup.

FIG. 11A is the representation of FIG. 4 showing placement of a tampon for drug delivery incorporating a distally placed suppository or gel capsule. FIG. 11B is a cross-sectional view of the embodiment shown in FIG. 11A, taken in the direction indicated by the arrows labeled 11B in FIG. 11A.

FIG. 12A is the representation of FIG. 4 showing placement of a tampon for drug delivery incorporating a distal foam cup comprising "fingers" for cervix enclosure. FIG. 12B is a side view of the distal porous foam cup.

FIG. 13 is the representation of FIG. 4 showing placement of a tampon drug delivery incorporating a scoop-shaped distal porous foam section.

FIG. 14 is a side view of the embodiment shown in FIG. 13.

FIG. 15 is a front view of the embodiment shown in FIG. 13.

FIG. 16 is the representation of FIG. 4 showing placement of a tampon for drug delivery incorporating distal fibers containing concentrated bisphosphonate drug formulation.

DEFINITIONS

Figure 1:
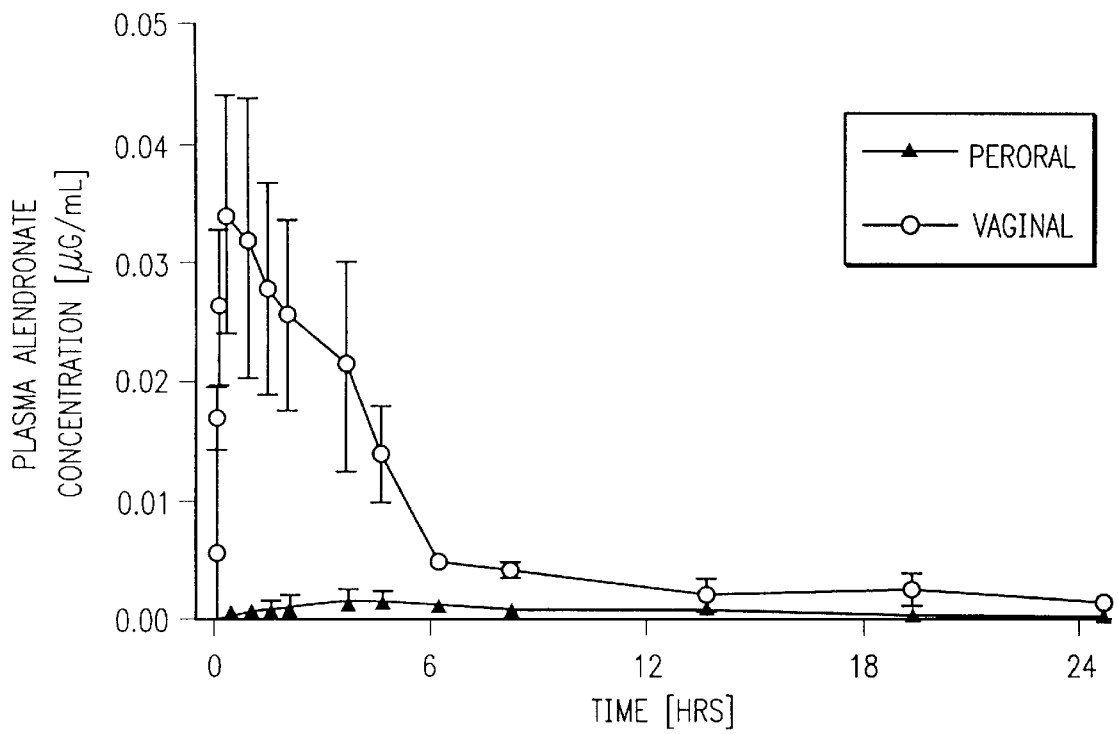
FIG. 1 illustrates concentrations-time profiles of alendronate in plasma ($\mu$g/ml) following oral intravenous and vaginal administration of a single dose of alendronate to female white New Zealand rabbit.

As described herein:

"Agent", "drug" or "compound" means a bisphosphonate selected from the group consisting of alendronate, clodronate, etidronate, pamidronate, tiludronate, ibandronate, risedronate, neridronate and any other bisphosphonate known now or which will become known in the future which has the same properties as bisphosphonates disclosed herein.

"BMD" means bone mineral density.

DETAILED DESCRIPTION OF THE INVENTION

This invention relates to a novel route of administration and delivery of bisphosphonates into systemic circulation. The new route of administration comprises intravaginal administration of bisphosphonates into vagina and transvaginal delivery of the bisphosphonates into the blood circulation. The invention improves systemic bioavailability of bisphosphonates by delivering these compounds to the circulation transvaginally in concentration ten to thirty times higher than those delivered orally.

The invention enables delivery of therapeutic concentrations of bisphosphonates needed for treatment of osteoporosis, Paget's disease and other bone and skeleton related diseases without occurrence of undesirable adverse side effects. Treatments of these diseases with the bisphosphonates are currently limited due to the side effects of these drugs which complicate their administration to the patient through oral routes and due to their poor absorption through the GI tract. Although these drugs may be administered intravenously, such administration is not convenient as it requires visit to the hospital or to the doctor's office.

The invention is based on inventors prior discovery that certain pharmaceutical agents may be conveniently and efficaciously delivered intravaginally to the vagina epithelium and mucosa and transvaginally to the uterus and/or to the blood circulation.

Intravaginal delivery comprises contacting the vaginal epithelium and mucosa with a composition comprising a therapeutically effective agent in admixture with a carrier, mucoadhesive agent, sorption enhancer or penetration promoter. Intravaginal delivery is achieved either directly by delivering the composition of the invention to the vagina or by delivering the composition of the invention to the vagina incorporated into a vaginal device. The composition or the device is placed into a close contact with or into a close proximity of the vaginal epithelium and mucosa wherein the agent is either released from the composition or released from the device and either directly or through the action of the mucoadhesive compound it comes into a contact with or adheres to the vaginal epithelium and mucosa where it penetrates the vaginal mucosa and is delivered transvaginally to the uterus and/or blood circulation by being absorbed or transported through vaginal mucosa. These findings are described by inventors in the U.S. Pat. No. 6,086,909 issued on Jul. 11, 2000 and in the U.S. application Ser. No. 09/079,897, allowed, both hereby incorporated by reference.

The current invention concerns a specific discovery that the problems encountered during oral delivery of bisphosphonates can be overcome by delivering the bisphosphonates to the blood circulation transvaginally via the vaginal mucosa. Transvaginal delivery of bisphosphonates through the vaginal mucosa significantly improves systemic bioavailability and greatly increases concentrations of bisphosphonates in the plasma.

Additionally, the invention concerns the discovery that bisphosphonates may be conveniently delivered to the circulation using pharmaceutical compositions comprising bisphosphonates in the form of suppositories, tablets, capsules, microcapsules, gels, foams, ointments, or creams or using medicated tampons, tampon-like devices, vaginal rings, sponges, cups, pessaries, or any other means for drug delivery suitable for intravaginal and transvaginal administration.

I. Vaginal Delivery of Bisphosphonates

The invention thus concerns a delivery of bisphosphonates into the blood circulation. These compounds are administered intravaginally into vagina and transferred through vaginal mucosa by the transvaginal route. Transvaginal absorption has been demonstrated for other drugs as previously described in the U.S. application Ser. No. 09/079,897, with direct uptake for many drugs equivalent to intravenous administration.

The transvaginal approach permits bisphosphonates to be administered as a gel, cream, foam, ointment, tablet, capsule, microcapsule, fluid, powder or suppository composition either directly or incorporated into the intravaginal device from which the composition is released, preferably in a sustained time release manner. The bisphosphonate is typically either attached to a lipophilic or hydrophilic carrier, depending on the bisphosphonate charge, and formulated in combination with a mucoadhesive agent to enhance adhesivity of the released compound to the vaginal mucosa and to assure contact with the vaginal mucosa. In order to enhance absorption of the bisphosphonate through the vaginal mucosa, an absorption (sorption) enhancer or penetration promoter for intravaginally administered compounds is utilized as another formulating agent.

A. Properties of Bisphosphonates

The bisphosphonates constitute a recently developed class of drugs for use in a variety of diseases of bone and calcium metabolism. Up-to-date there are three generations of bisphosphonates, as shown below.

Bisphosphonates are synthetic analogs of pyrophosphates characterized by phosphorus-carbon-phosphorus backbone that renders them resistant to hydrolysis. The properties of the bisphosphonates vary based on different substitutions at the carbon atom of the phosphorus-carbon-phosphorus backbone.

A group of currently known bisphosphonates include alendronate, clodronate, etidronate, pamidronate, tiludronate, ibandronate, zoledronate, olpadronate, residronate and neridronate. Their chemical formulae are seen below.

First generation

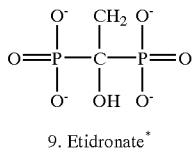

9. Etidronate*

Second generation

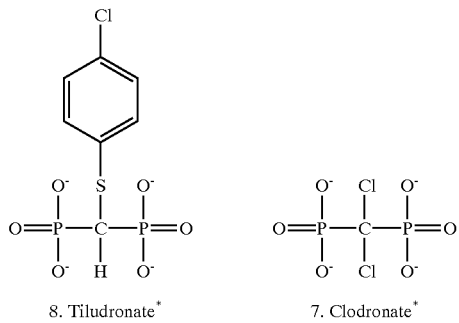

8. Tiludronate*  7. Clodronate*

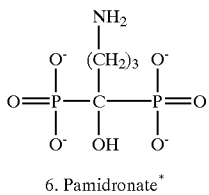

6. Pamidronate*

Third generation

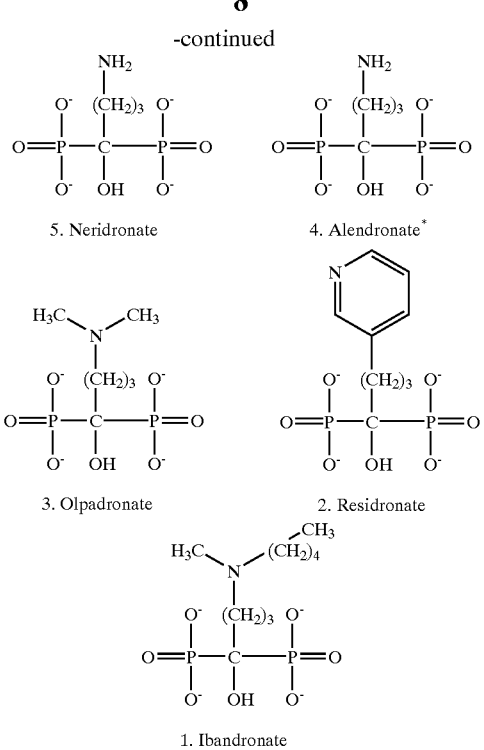

5. Neridronate  4. Alendronate*

3. Olpadronate  2. Residronate

1. Ibandronate

1. Clinical Use of Bisphosphonates

Bisphosphonates are analogues of pyrophosphates and like them, are strongly bound to hydroxyapatite on the bone surface. Biophosphonates are stable and reduce and inhibit activity of osteoclasts, cells functioning in the absorption and removal of osseous tissue.

The clinical use of biophosphonates is based on their ability to inhibit bone resorption. Thus, the main indications for their use concern diseases with high bone remodeling, such as Paget's disease of bone, osteoporosis, metastatic bone diseases, and malignant and nonmalignant hypercalcemia.

The primary effect of bisphosphonates is the inhibition of bone resorption through cellular mechanisms that effect osteoclast attachment to bone, osteoclast precursor differentiation, and osteoclast survival. The anti-resorptive effect of bisphosphonates is also mediated through effects on the osteoblast.

Bisphosphonates also appear to mediate the anti-cancer effects by modifying the bone surface, altering the bone microenvironment, inhibiting specific enzymatic pathways, and inducing apoptosis in osteoclast and tumor cells. The role of bisphosphonates as anti-cancer agents continues to expand and new and more potent bisphosphonates are being introduced into clinical practice.

Doses of bisphosphonates shown to inhibit bone resorption, however, are difficult to achieve orally, due to their poor absorption, and potential gastrointestinal irritability. Therefore, their oral use is rather limited.

Despite difficulties encountered with their oral administration, bisphosphonates are very potent drugs when delivered in therapeutic doses. They have a unique spectrum of potency and a mechanism of action. The parent compound, etidronate, was first used in multicentered trials for the treatment of primary osteoporosis and showed success in increasing bone density and controlling fracture rates. The recently approved drug alendronate which is a more potent agent than etidronate, produces a greater increase in bone density, and decreases the number and severity of fractures. Oral and intravenous pamidronate have similar positive effects on bone density. Studies with tiludronate, risedronate, and clodronate show similar effects as therapeutic agents.

2. Adverse Reactions of Orally Administered Bisphosphonates

As discussed above in the Background section, despite their potential benefits in treating bone disorders, the full therapeutic potential has not been achieved because of severe adverse reactions, lack of efficacy and inconvenient regimen required for bisphosphonate oral administration. The adverse reactions include irritation, ulceration or inflammation of esophagus and stomach. Lack of efficacy is evidenced by poor absorption of bisphosphonates through the intestinal tract resulting in bioavailability of less than 1% of the administered oral dose. The strict regimen required for bisphosphonates oral administration results in great inconvenience for a patient resulting in abandonment of this treatment by many patients.

Until these problems with oral administration will be solved, bisphosphonates will not become drugs of choice for treatment and prevention of osteoporosis and related bone diseases. The current invention provides an alternative method to the oral administration by delivering these drugs transvaginally to the blood in amounts which are more than fifteen times higher than those delivered orally.

3. Transvaginal Delivery of Bisphosphonates

The transvaginal method eliminates the local gastrointestinal irritation and subsequent ulceration of esophagus and stomach, it is much more efficacious than the oral administration and does not involve dietary or time restrictions which are necessary for oral delivery.

The successful transvaginal administration of biphosphonates depends on their specific properties, such as pH, absorption through mucosa, effectiveness and lack of irritability and toxicity. In this respect, the pK of the bisphosphonate compounds has been found ideal for vaginal pH levels. Bisphosphonates have also been found to be compatible with the absorption enhancers and mucoadhesive agents which have been demonstrated with other compounds to promote highly successful delivery of the drug to the vascular system. These agents have been found equally effective for enhancement of bisphosphonate absorption.

Transvaginally delivered bisphosphonates have shown a great therapeutic potential with smaller amounts of these drugs necessary to obtain full therapeutic action. Vaginally delivered bisphosphonates have been found to be at least fifteen times more effective than orally administered bisphosphonate.

The method of the invention for transvaginal delivery includes formulating the active pharmaceutical agent, in this case, one of the bisphosphonates, in a reservoir form for daily dosing of from about 0.001 mg to about 2000 mg/day of the selected bisphosphonate, typically in combination with a carrier, preferably the lipophilic carrier, a mucoadhesive, a solubilizer and/or a penetration enhancer. Due to its excellent vaginal absorption, the bisphosphonate formulation is administered daily, weekly, monthly or even quarterly, depending on the intended use.

B. Types of Bisphosphonates

Generally, all bisphosphonates assert a specific effect on bone structure and formation. Each of the known bisphosphonates has been investigated and the following properties have been described.

1. Alendronate

Alendronate is commercially available from Merck & Co., Inc., Rahway, N.J. as alendronate sodium under the product name FOSAMAX®.

a. Therapeutic Benefits of Alendronate

Alendronate increases bone mineral density (BMD), prevents radiographically defined (morphometric) vertebral fractures and positively affects morphometric as well as clinically evident fractures in postmenopausal women with low bone mass.

b. Disadvantages of Oral Administration

When administered orally, alendronate has been shown to be poorly absorbed though the gastrointestinal tract and to have a bioavailability of less than 1%. When administered in doses ranging between 5–40 mg to women fasting overnight and administered orally 2 hours before first meal of the day its bioavailability has been found to be as low as 0.7%. In men, this value has been reported to be even lower at 0.59%.

The absorption and bioavailability is reduced even further by additional 40% if the compounds are administered 30–60 minutes before the first meal of the day. If administered concurrently with the meal or two hours afterward, the absorption and the drug bioavailability is negligible. Even coffee and orange juice intake results in additional reduced absorption by about 60%.

Additionally to poor absorption and bioavailability, alendronate causes severe irritation of the mucosa of the upper GI tract, especially the esophagus, with development of frequent bleeding and ulceration. These symptoms may be reduced by taking at least two cups of water with each tablet at least 60 minutes before the meal. This regimen, however, understandably proves to be difficult and inconvenient for dosing patients. The patients are also warned not to chew the tablets because of oral or pharyngeal ulcerations. The concurrent use of aspirin and other NSAID's seems to increase the GI symptoms and ulceration.

Up to 10% of the patients in a one-year, highly controlled clinical trial have been reported to have stopped using FOSAMAX® because of side effects. Treatment discontinued rates have proven to be much larger (>50%) in actual clinical use of the drug on a non-protocol basis.

As is evident from the above, although alendronate is a very good pharmaceutical agent for treatment of osteoporosis and Paget's disease, its use is necessarily limited due to its poor absorption and bioavailability and not the least by the development of severe health complications.

c. Transvaginal Delivery of Alendronate Therapeutic Formulation

The current invention provides alendronate in a pharmaceutical composition suitable for intravaginal administration either directly in a form of a vaginal suppository, foam, cream, tablet, capsule, ointment, gel or microcapsules or indirectly to be administered via an intravaginal device. Alendronate daily dose is from about 1 to about 40 mg/day administered once, twice or as many times/day, week, month or quarterly, as needed. The formulation is, preferably, in sustained release form to provide a continuous and sustained release of the drug from the formulation. However, to provide a daily supply of the drug, the drug may be formulated for a rapid release and transvaginal absorption.

2. Clodronate

Clodronate is commercially available. Currently, clodronate is administered intravenously or orally.

a. Therapeutic Benefits of Clodronate

Clodronate has been shown to inhibit increases in bone resorption and to prevents bone loss due to the menopause and during immobilization. Short-term and long-term studies indicate that clodronate stops bone loss at the lumbar spine in patients with vertebral osteoporosis. Treatment with clodronate induces a gain in bone mass, especially in the spine. Even high doses of clodronate do not impair the mineralization of bone, making it suitable for long-term use in osteoporosis.

Clodronate treatment has also been shown to decrease bone turnover and to attenuate cancer-related bone morbidity. In addition, clodronate increased BMD in apparently unaffected bone of women with relapsing breast cancer.

b. Disadvantages of Oral Administration

As is evident from the above, clodronate is a potent pharmaceutical agent for treatment of osteoporosis and Paget's disease. However, as with other bisphosphonates, it shows poor absorption and bioavailability as well as irritability of esophagus and, therefore, its use is necessarily limited due to development of adverse reactions.

c. Transvaginal Delivery of Clodronate Therapeutic Formulation

The current invention provides clodronate in a pharmaceutical composition suitable for intravaginal administration either directly in a form of a vaginal composition such as vaginal suppositories, creams, foams, tablets, capsules ointments, gels or microcapsules or indirectly as a composition incorporated into an intravaginal device of the invention to be administered via said intravaginal device. Clodronate daily dose is from about 100 to about 1600 mg/day administered once, twice or as many times/day, week, month or quarterly, as needed. The formulation is, preferably, in sustained release form to provide a continuous and sustained release of the drug from the formulation. However, to provide a daily supply of the drug, the drug may be formulated for a rapid release and transvaginal absorption.

3. Etidronate

Etidronate is commercially available from Procter & Gamble.

a. Therapeutic Benefits of Etidronate

Etidronate is suitable for treatment of patients with corticosteroid induced osteoporosis as it prevents loss of vertebral bone density in these patients. Therapy with cyclical etidronate plus ergocalciferol prevented glucocorticoid-induced bone loss and even increased lumbar spine and femoral neck BMD in postmenopausal women commencing glucocorticoid therapy.

After one year of open-label treatment, patients previously treated with etidronate maintained bone mass, and occurrence of vertebral fracture rates in all groups were lower than in any other study period. Three years of intermittent cyclic etidronate therapy produced significant increases in spinal and hip bone density, with a significant reduction in vertebral fracture rates in patients at higher fracture risk. Maintenance of bone mass and low fracture rate were observed when etidronate was continued for another year.

b. Disadvantages of Oral Administration

Although there were no serious adverse effects observed from etidronate use, and etidronate was found to be a potent pharmaceutical agent for prevention and treatment of osteoporosis and loss of vertebral bone density, as with other bisphosphonates, it shows low absorption from GI tract and bioavailability. Therefore, its use is necessarily limited and the improvement of bioavailability would improve its therapeutic efficacy.

c. Transvaginal Delivery of Etidronate Therapeutic Formulation

The current invention provides etidronate in a pharmaceutical composition suitable for intravaginal administration either directly as an intravaginal composition in a form of vaginal suppositories, creams, tablets, ointments, gels or microcapsules or indirectly to be administered via an intravaginal device of choice, as described below. Etidronate daily dose is from about 7.5 to about 750 mg/day administered once, twice or as many times a day, week, month or quarterly, as needed. The composition is, preferably, formulated in a sustained release form to provide a continuous and sustained release of the drug from the composition. However, to provide a daily supply of the drug, the drug may be formulated for a rapid release and transvaginal absorption.

4. Pamidronate

Pamidronate (aminohydroxypropylidine bisphosphonate, APD) is commercially available from Novartis, Switzerland.

a. Therapeutic Benefits of Pamidronate

Pamidronate is an effective agent for treatment of Paget's disease of bone, and it is also effective for treatment of osteoporosis. Long-term treatment with an orally administered pamidronate overcomes bone loss and increases bone mass when compared with placebo and may be suitable for the treatment of patients with rheumatoid arthritis. Long-term uninterrupted treatment of patients with osteoporosis with oral pamidronate is associated with increases in bone mineral content (BMC) of the lumbar spine and with an additional effect of the treatment on skeletal tissue.

Administration of suppressive doses of the pamidronate to patients with excessive osteoclastic resorption is followed by transient decreases in serum calcium and increases in parathyroid hormone (PTH) concentrations. Chronic pamidronate therapy thus may stimulate PTH secretion, which in turn has been previously shown to have anabolic effects on the skeleton.

b. Disadvantages of Oral Administration

Pamidronate is known to cause esophagitis in treated patients and although it is a potent pharmaceutical agent for prevention and treatment of Paget's disease, osteoporosis and for increasing bone mass, as with other bisphosphonates, it shows poor absorption and bioavailability as well as irritability and ulceration of esophagus and, therefore, its use is necessarily limited due to development of these adverse reactions.

c. Transvaginal Delivery of Pamidronate Therapeutic Formulation

The current invention provides pamidronate in a pharmaceutical composition suitable for intravaginal administration. The composition is provided either directly in a form of a vaginal suppository, cream, tablet, capsule, ointment, gel or microcapsules or indirectly to be administered via an intravaginal device. Pamidronate daily dose is from about 1 to about 20 mg/day administered once, twice or as many times/day, week, month or quarterly, as needed. The formulation is, preferably, in sustained release form to provide a continuous and sustained release of pamidronate from the formulation. However, to provide a daily supply of pamidronate, it may be formulated for a rapid release and transvaginal absorption.

5. Tiludronate

Tiludronate (tiludronic acid disodium salt) is commercially available from Sanofi, France.

a. Therapeutic Benefits of Tiludronate

Tiludronate was shown to be effective in reducing bone resorption in several metabolic bone diseases without inducing mineralization defects. The clinical development of tiludronate for the treatment of Paget's disease of bone have shown that tiludronate is equally suitable for treatment of osteoporosis. Osteoporosis becomes a major indication for tiludronate.

b. Disadvantages of Oral Administration

As is evident from the above, although tiludronate is a very good pharmaceutical agent for treatment of osteoporosis and Paget's disease, its use is necessarily limited due to its poor absorption and bioavailability and not the least by the development of adverse reactions.

c. Transvaginal Delivery of Tiludronate Therapeutic Formulation

The current invention provides tiludronate in a pharmaceutical composition suitable for intravaginal administration either directly in a form of a vaginal suppository, cream, tablet, ointment, gel or microcapsules or indirectly by incorporation, said composition into the intravaginal device of the invention. Tiludronate daily dose is from about 2 to about 400 mg/kg, administered once, twice or as many times/day, week, month or quarterly, as needed. The formulation is, preferably, in sustained release form to provide a continuous and sustained release of the drug from the formulation. However, to provide a daily supply of the drug, the drug may be formulated for a rapid release and transvaginal absorption.

6. Ibandronate

Ibandronate is commercially available.

a. Therapeutic Benefits of Ibandronate

A new, third generation bisphosphonate ibandronate is preferentially useful for treatment of postmenopausal osteoporosis. Ibandronate treatment increases bone mass in all skeletal regions in a dose dependent manner with 2.5 mg/daily being the most effective dose. Ibandronate treatment reduces bone turnover to premenopausal levels and is well tolerated.

b. Disadvantages of Oral Administration

As is evident from the above, although ibandronate is a potent pharmaceutical agent for treatment of osteoporosis and Paget's disease, its use is necessarily limited due to its poor absorption and bioavailability.

c. Transvaginal Delivery of Ibandronate Therapeutic Formulation

The current invention provides ibandronate in a pharmaceutical composition suitable for intravaginal administration either directly in a form of a vaginal suppository, cream, tablet, ointment, gel or microcapsules or indirectly to be administered via an intravaginal device. Ibandronate daily dose is from about 0.5 mg to about 50 mg/day administered once, twice or as many times as needed. The formulation is, preferably, in sustained release form to provide a continuous and sustained release of the drug from the formulation. However, to provide a daily supply of the drug, the drug may be formulated for a rapid release and transvaginal absorption.

7. Neridronate

Neridronate is commercially available.

a. Therapeutic Benefits of Neridronate

Neridronate is a third generation amino-bisphosphonate useful for treatment and prevention of osteoporosis as well as collagen disease.

b. Disadvantages of Oral Administration

Although neridronate is an effective pharmaceutical agent for treatment of osteoporosis and collagen related diseases, its use is limited due to its poor absorption and bioavailability.

c. Transvaginal Delivery of Neridronate Therapeutic Formulation

The current invention provides neridronate in a pharmaceutical composition suitable for intravaginal administration either directly in a form of a vaginal suppository, cream, tablet, ointment, gel or microcapsules or indirectly to be administered via an intravaginal device. Neridronate preferred daily dose is from about 0.01 to about 0.7 mg/kg/day administered once, twice or as many times/day as needed. The formulation is, preferably, in sustained release form to provide a continuous and sustained release of the drug from the formulation. However, to provide a daily supply of the drug, the drug may be formulated for a rapid release and transvaginal absorption.

8. Risedronate

Risedronate is commercially available from Procter & Gamble as the product ACTONEL.

a. Therapeutic Benefits of Risedronate

Risedronate is a third generation bisphosphonate useful for treatment and prevention of osteoporosis.

b. Disadvantages of Oral Administration

Although risedronate is an effective pharmaceutical agent for treatment of osteoporosis and related diseases, its use is limited due to its rapid absorption resulting in unpredictable bioavailability.

c. Transvaginal Delivery of Risedronate Therapeutic Formulation

The current invention provides risedronate in a pharmaceutical composition suitable for intravaginal administration either directly in a form of a vaginal suppository, cream, tablet, ointment, gel or microcapsules or indirectly to be administered via an intravaginal device. Risedronate preferred daily dose is from about 1 to about 80 mg/day administered once, twice or as many times/day as needed. The formulation is, preferably, in sustained release form to provide a continuous and sustained release of the drug from the formulation. However, to provide a daily supply of the drug, the drug may be formulated for a rapid or slow release and transvaginal absorption.

Two additional bisphosphonates, namely zoledronate and olpadronate are currently under development for similar therapeutic use as described for other bisphosphonates.

C. Pharmacokinetics of Vaginal Delivery of Bisphosphonates

Vaginal delivery of alendronate was investigated in the rabbit model. Since the systemic bioavailability of alendronate, a potent antiosteolytic bisphosphonate, is generally below 1% when the dose is administered via the oral route, the objective of this study was to determine whether the delivery of alendronate across the vaginal mucosa has the potential to significantly improve the systemic bioavailability of this drug.

Figure 2:
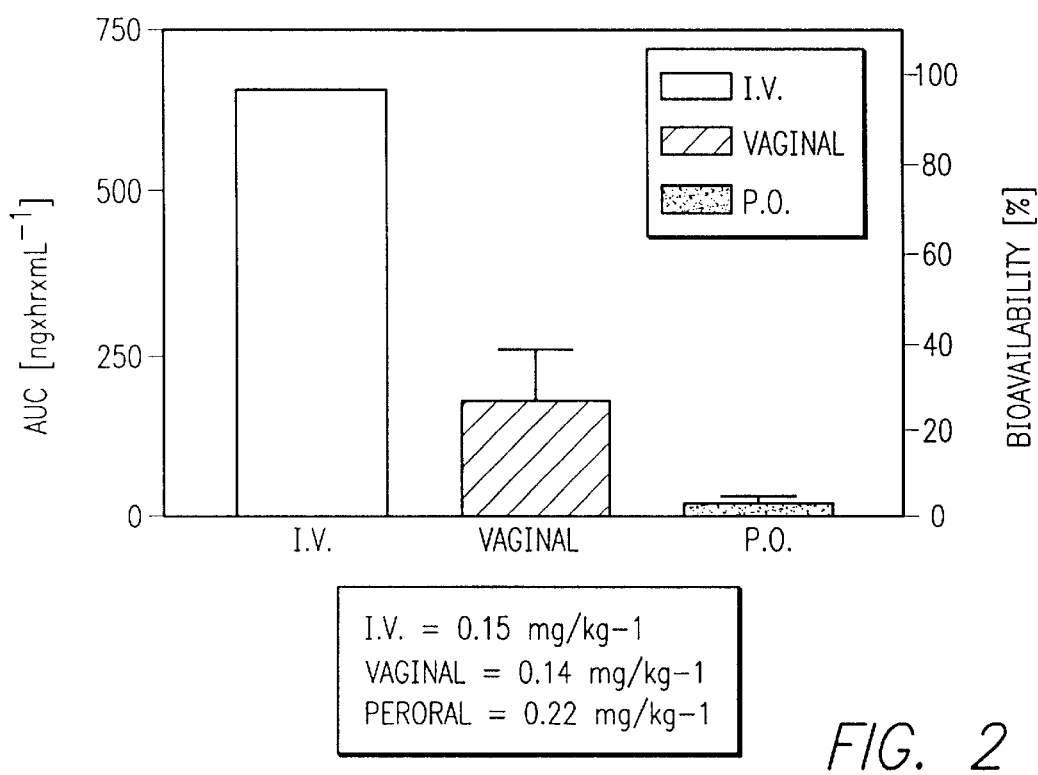
FIG. 2 represents bioavailability, in percent, of alendronate in plasma following an oral, intravenous or vaginal administration of alendronate to female white New Zealand rabbit.

Plasma pharmacokinetics of alendronate were determined in anesthetized female white New Zealand rabbits after intravenous, vaginal, and peroral administration (dose= 0.14–0.22 mg/kg). For analytical purposes, each dose was supplemented with a trace amount of [$^{14}$C] alendronate. Model-independent pharmacokinetic parameters were calculated using WinNonlin form plasma concentrations of alendronate collected for 24 hours. Results are illustrated in FIGS. 1 and 2 and in Table 1.

TABLE 1

Pharmacokinetic Parameters of Alendronate in New Zealand Rabbits Following Intravenous, Vaginal, and Peroral Administration

| Parameter | Intravenous | Vaginal | Peroral |
| --- | --- | --- | --- |
| Dose [mgxkg$^{-1}$] | 0.15 | 0.14 | 0.22 |
| $c_{max}$ [ngxmL$^{-1}$] | N/A | 34.0 ± 14.4 | 1.8 ± 1.2 |
| $T_{max}$ [hr] | N/A | 0.5 ± 0.1 | 4.8 ± 2.0 |
| AUC [ngxhrxmL$^{-1}$] | 652.7 | 180.0 ± 82.4 | 18.2 ± 12.1 |
| $t_{1/2}$ [hr] | 13.4 | 19.6 ± 3.4 | 17.4 ± 5.1 |
| F | 100 | 30.1 ± 13.4 | 2.0 ± 1.3 |

Pharmacokinetic parameters were calculated from plasma drug concentrations using the model-independent analysis module of WinNonlin.

Table 1 lists pharmacokinetic parameters observed in plasma of white New Zealand rabbits following the intravenous, intravaginal and oral administration of alendronate in doses 0.15 mg/kg for intravenous, 0.14 mg/kg for vaginal and 0.22 mg/kg for oral route of administration. Table 1 further shows maximal plasma concentration ($c$max), area under the curve (AUC) in ng/hr/ml$^{-1}$, an apparent half-life ($t_{1/2}$/hr) and bioavailability (F).

As seen in Table 1, after intravenous administration of alendronate in a saline solution, alendronate rapidly disappeared from the vascular system with a terminal half-life of 13.4 hours. This is consistent with earlier observations in various other species and relates to the high affinity of this drug to the bone.

When delivered vaginally using a suppository that was formulated with 25% (w/w) TRANSCUTOL®, plasma concentrations of alendronate rapidly increased to reach a maximum around 0.5 hr, as seen in FIG. 1. From the area under the plasma concentration time curve (AUC), the mean absolute bioavailability that was calculated for this new route of administration was 30.1%. The terminal half-life of alendronate following vaginal administration was close to 20 hr. However, within statistical confidence, this value is not significantly different from the corresponding terminal half-life calculated from the intravenous data.

In comparison, the mean absolute bioavailability of alendronate in rabbits following oral administration was only 2%. This is in agreement with published data for dogs and monkeys.

From these results, it is clear that vaginal delivery of alendronate is significantly more effective than oral delivery. To achieve plasma concentrations of alendronate following vaginal administration that are equivalent to the drug concentrations measured following oral administration, approximately 7% of the oral dose would be sufficient for vaginal administration. As a substantial benefit for the patient, because of the 20–30% increased absorption into the systemic circulation by the vaginal delivery, the intravaginally delivered bisphosphonates may be delivered daily, bi-daily, weekly, monthly or even quarterly. The vaginal administration of alendronate can significantly reduce the severe side effects that are characteristic for the drug class of bisphosphonate.

FIG. 1 shows concentration-time profiles of alendronate in plasma following vaginal and oral administration of a single dose ranging from 0.14 to 0.22 mg/kg to female white New Zealand rabbits. All studies were performed in duplicate and the values given are average±SEM.

As seen from FIG. 1, while peroral administration of 0.22 mg/kg of weight did not raise concentrations (μg/ml) of alendronate in plasma during 24 hours, or such increase was very low and occurred only during the first six hours, resulting in only about 2% bioavailability of alendronate, the vaginal administration resulted in rapid increase of alendronate in plasma, reaching its peak in less than one hour after administration and decreasing slowly during 24 hours, reaching bioavailability values of about 30%. About fifteen times more alendronate was present and available in plasma following the vaginal delivery when compared to the levels of alendronate observed following the orally administered alendronate.

These results are unexpected and surprising and confirm that the vaginal delivery is efficacious and combined with elimination of adverse reactions observed during oral delivery, the vaginal delivery is much better way to administer bisphosphonates.

FIG. 2 is a graphical illustration of bioavailability (%) of alendronate observed following the oral (2%), vaginal (30%) and intravenous (close to 100%) administration of alendronate in 0.22, 0.14 and 0.15 mg/kg doses, respectively.

As seen from the above results, the vaginal delivery is clearly superior to the oral delivery and eliminates all adverse effects accompanying the oral administration. Because of the unique formulation consisting of the mucoadhesive agents, penetration promoters and a drug specific carrier, the poor absorbance through the GI tract mucosa is overcome and the bisphosphonate is delivered in a therapeutically effective amount through the vaginal mucosa directly to the systemic circulation.

According to the invention, bisphosphonates which are brought into contact with the vaginal mucosa and epithelium of a female increase the drug bioavailability. The method for intravaginal and transvaginal delivery of bisphosphonates is eminently suitable for the treatment of osteoporosis associated with aging, Paget's disease, other diseases of bone and skeleton, bone fractures and bone metastasis due to a variety of cancers.

II. Compositions, Formulation and Devices for Vaginal Delivery

The primary purpose of this invention is to enhance the systemic delivery of a series of bisphosphonates which have poor bioavailability and a high level of gastrointestinal toxicity, both for treating and preventing the osteoporosis and related diseases of bone and skeleton. Examples of the drug delivery system are the compositions comprising the bisphosphonate such as bioadhesive microparticles, creams, lotions, foams, ointments, solutions, and gels alone or incorporated into a device including vaginal rings, pessaries, tablets, vaginal suppositories, vaginal sponges, bioadhesive tablets.

A. Compositions for Intravaginal and Transvaginal Delivery of Bisphosphonates Compositions for intravaginal and transvaginal administration and delivery typically comprise a bisphosphonate drug present in about 0.001 to about 2000 mg, depending on the particular bisphosphonate, a lipophilic or hydrophilic, preferably the lipophilic carrier present in about 40–95%, preferably about 60–85% (w/w), mucoadhesive agent present in about 5–25%, preferably from about 3–10%, most preferably from 5–10% (w/w), solubilizer present in about 5–25%, preferably from about 3–15%, and penetration enhancer or sorption promoter present in 5–25%, preferably from about 5–20% and most preferably from about 10 to about 20% (w/w) concentration.

Other excipients, such as additives, fillers, coloring agents, or other pharmaceutically acceptable and/or therapeutically effective compounds may also be added to the compositions of the invention.

1. Pharmaceutical Agents

A pharmaceutical agent suitable for intravaginal delivery is any bisphosphonate known now or discovered later which may be formulated with a drug delivery system according to the invention.

Pharmaceutical agents for use in the invention are absorbable through the vaginal mucosa into the circulation system. The pharmaceutical agent is preferably selected from the group consisting of bisphosphonates alendronate, risedronate, clodronate, pamidronate, etidronate, siludronate, neridronate and ibandronate.

2. Excipients and Carriers

A composition for intravaginal administration typically comprises a suitable biocompatible excipient for formulating the bisphosphonate, which excipient includes a lipophilic carrier, a hydrophilic carrier, a mucoadhesive agent and a penetration enhancer.

In order to achieve desirable drug release, the active ingredient i.e. a bisphosphonate is incorporated into an excipient (i.e., vehicle or carrier) for which the drug has low affinity. Hence, hydrophilic drugs are incorporated into lipophilic carriers, and lipophilic drugs will be incorporated into hydrophilic carriers.

Preferred lipophilic carriers for use with hydrophilic drugs include semi-synthetic glycerides of saturated fatty acids, particularly fatty acids of eight to eighteen carbons, such as SUPPOCIRE® AS2 (Gattefosse, Westwood, N.J.) and other suitable hard fats and carriers.

Preferred hydrophilic carriers, for promoting synergistic drug delivery, include polyethylene glycol or mixtures thereof, such as PEG 6000/PEG 1500, or PEG 6000/PEG 1500/PEG 400, or PEG 6000/PEG 400 (Sigma/Aldrich, St. Louis, Mo.).

The system of the invention preferably also comprises a mucoadhesive agent to bring the released drug in solution into prolonged, close contact with the mucosal surface. The muco-adhesive agent is preferably a polymer such as an alginate, pectin, or a cellulose derivative. Hydroxypropyl methylcellulose is particularly preferred for use in the present invention.

The system of the invention may also additionally include a penetration enhancer or sorption promoter to enhance permeation of the drug across the uterine mucosal barrier. Preferred sorption promoters include nonionic surface active agents, bile salts, organic solvents, interesterified stone oil, particularly ethoxydiglycol commercially available as TRANSCUTOL® from Gattefosse, and interesterified stone oil, commercially available as LABRAFIL® M 1944CS from Gattefosse.

Additionally, the composition may comprise a solubilizer, such as Tween, a polyoxethylene castor oil derivative, cyclodextrine, polyoxethylene alkyl ester, glyceryl monostearate, lecithin, poloxamer, polyoxethylene stearate and a sorbitan ester.

B. Drug Delivery Systems

The vaginal drug delivery systems of the invention provides a sustained and controlled delivery of the drug to the vaginal epithelium.

9. Types of Delivery Systems

The delivery system can be a solid object delivery system such as a tampon, tampon-like device, vaginal ring, cup, pessary, tablet or suppository. Alternatively, it can be a composition in the form of paste, cream, ointment or gel having a sufficient thickness to maintain prolonged contact with vaginal epithelium. Alternatively, it can be a coating on a suppository wall or a sponge or other absorbent material impregnated with a liquid drug containing solution, lotion, or suspension of bioadhesive particles, for example. Any form of drug delivery system which will effectively deliver the treatment agent to the vaginal endothelium is intended to be included within the scope of this invention.

For purposes of simplifying the description of the invention and not by way of limitation, tampon and suppository drug delivery systems will be described hereinafter, it being understood that all effective delivery systems are intended to be included within the scope of this invention.

2. Controlled Release Drug Delivery

The controlled release drug delivery system must be capable of controlled release of a drug into the vagina over several hours or more. For example, during the menstrual cycle, the pH of the vagina changes and this fact must be taken in consideration when the delivery system is designed. Drug delivery systems with buffers to enhance absorption are included in the present invention. The delivery system must be capable of functioning in the presence of menstrual blood. Additionally, the system, for example the tampon, should be easily removable, for example, attached to a string or tape.

For controlled release systems, solid phase drug carriers are preferred, because carriers that dissolve or can be diluted out can be carried away by menstrual blood. Advantages of a solid carrier include: 1) no increase in messiness; 2) carrier will not promote bacterial overgrowth with menstrual blood present; 3) carrier may be washable or reusable (e.g., vaginal ring).

3. Bioadhesive Systems

Bioadhesive microparticles constitute still another intravaginal drug delivery system suitable for use in the present invention.

The bioadhesive systems use hydroxypropyl cellulose and polyacrylic acid. They release drugs for up to five days once they are placed in the appropriate formulation. This system represents a multi-phase liquid or semi-solid preparation which does not seep from the vagina as do most current suppository formulations. The microparticles cling to the wall of the vagina and release the drug over a several hour period of time. Many of these systems were designed for nasal use, as described in U.S. Pat. No. 4,756,907, incorporated herein by reference, but can be easily modified for use in the vagina. The bioadhesive system may comprise microspheres filled with the bisphosphonate and may contain a surfactant for enhancing uptake of the drug. The microparticles have a diameter of 10–100 μm and can be prepared from starch, gelatin, albumin, collagen, or dextran according to methods known in the art.

C. Formulations

Formulations of the invention are specific for intravaginal delivery of the composition of the invention. The formulation is, therefore, directed to specific requirements of the intravaginal release of the drug from the composition, for bringing the drug into a close proximity or in contact with the vaginal epithelium and mucosa and for promoting the penetration absorption, transfer or transport of the drug through the vaginal mucosa.

Typically, therefore, the composition will be formulated with a lipophilic or hydrophilic carrier suitable for the selected bisphosphonate and the mucoadhesive agent which increases contact with vaginal epithelium and enables adhesion of the drug or drug carrier complex to the vaginal mucosa. Additionally, since the penetration, absorption, transfer or transport of the bisphosphonate to the systemic circulation is mandatory in this invention, the composition will also be formulated with a penetration enhancer or sorption promoter to enable such penetration, absorption, transfer or transport through the mucosa.

3. Representative Formulation

The formulations listed below have been prepared and tested, but are listed here only for purposes of illustrating the compositions of the invention. They are not intended to be in any way, limiting and all formulations falling within the scope of the ranges listed above are intended to be within the scope of the invention.

The intravaginal formulation of the invention comprises, in one embodiment of the invention, a bisphosphonate between about 0.01 and 10%, by weight, and about 90–99% of the excipient comprising between about 60 to 90%, by weight, lipophilic carrier, between about 5 to 25%, by weight, muco-adhesive agent, and between about 5 to 25%, by weight, penetration enhancer.

In another embodiment of the invention, the formulation comprises a bisphosphonate about 0.01–10%, by weight, and about 90–99% the excipient comprising between about 60 to 90%, by weight, hydrophilic carrier, between about 5 to 25%, by weight, mucoadhesive agent, and between about 5 to , by weight, penetration enhancer.

In another embodiment of the invention, the formulation comprises a standard fragrance free lotion sold under the trademark JERGENS® lotion in continuation with about 0.01–5% of a bisphosphonate.

In another embodiment, the formulation comprises about 0.01–5%, by weight, of a bisphosphonate, and the biocompatible excipient, such as glycerin, mineral oil, polycarbophil, carbomer 934P, hydrogenated palm oil, glyceride, sodium hydroxide, sorbic acid, and purified water.

In another embodiment of the invention, the formulation comprises about 0.01–5% bisphosphonate formulated into a vaginal suppository which includes 75% of a lipophilic carrier SUPPOCIRE® AS2, 10% of muco-adhesive hydroxypropyl methylcellulose, and 15% of penetration enhancer TRANSCUTOL®.

2. Other Formulation

The bisphosphonate can be incorporated into creams, lotions, foams, paste, ointments, and gels which can be applied to the vagina using an applicator. Processes for preparing pharmaceuticals in cream, lotion, foam, paste, ointment and gel formats can be found throughout the literature. An example of a suitable system is a standard fragrance free lotion formulations containing glycerol, ceramides, mineral oil, petrolatum, parabens, fragrance and water such as the product sold under the trademark JERGENS® (Andrew Jergens Co., Cincinnati, Ohio). This formulation was described in the Abstract No.97,051, North American Menopause Society, Boston, Mass., September (1997) for transcutaneous delivery of estradiol and progesterone.

Suitable other nontoxic pharmaceutically acceptable systems for use in the compositions of the present invention will be apparent to those skilled in the art. This includes all pharmaceutical formulations and examples described in *Remington's Pharmaceutical Sciences*, 19th Edition, A.R. Gennaro, Ed., (1995), *The Theory and Practice of Industrial Pharmacy*, Lachman, Lieberman and Kanig and *Pharmaceutical Dosage Forms*, Liberman and Lachman.

The choice of suitable carriers will depend on the exact nature of the particular vaginal dosage form desired, e.g., whether the active ingredients(s) is/are to be formulated into a cream, lotion, foam, ointment, paste, solution, or gel, as well as on the identity of the active ingredient(s).

3. Process for Preparation of Bisphosphonates Formulations

In a general method for preparing a formulation including a hydrophilic drug, the lipophilic carrier is melted at 45–50° C. in a heated vessel. The mucoadhesive agent is added to the carrier with stirring. The preferred hydrophilic drug is dissolved in the sorption promoter, and the drug/sorption promoter solution is added to the carrier/muco-adhesive agent solution. The final formulation is poured into molds of the desired size and shape, which are then placed in a refrigerator at 4–6° C.

Preferred formulations for lipophilic drugs comprise between about 50–90% hydrophilic carrier, between about 5–25% muco-adhesive agent, and between about 5–25% sorption promoter.

In a general method for preparing a formulation including a lipophilic drug, the hydrophilic carrier is melted at an appropriate temperature for the particular PEG used in a heated vessel. The muco-adhesive agent is added to the carrier with stirring. The preferred lipophilic drug is dissolved in the sorption promoter, and the drug/sorption promoter solution is added to the carrier/muco-adhesive agent solution. The final formulation is poured into molds of the desired size and shape, which are then placed in a refrigerator at 4–6° C.

D. Devices for Transvaginal Drug Delivery

The device of the invention can be in the form of, for example, a tampon-like device, vaginal ring, pessary, tablet, paste, suppository, vaginal sponge, bioadhesive tablet, bioadhesive microparticles, incorporated with a composition comprising a bisphosphonate. Each of these systems is discussed below.

1. A Tampon or Tampon-Like Device

In one embodiment, the invention provides a tampon device for delivering a pharmaceutical agent to the uterus comprising an absorbent vaginal tampon having a proximal end and a distal end. A cup-shaped porous foam portion at the distal end fits around the cervix of the uterus and contains a pharmaceutical agent for delivery to the cervix. The device may also include a nonabsorbing axial tube having a distal opening and extending through the porous foam cup into the tampon for conducting blood flow to the absorbent material. A retrieval string or tape connected to the tampon device is also included. The absorbent vaginal tampon may contain any of the above-mentioned drugs and be used as a medicated tampon for individual drug or drug combination delivery.

In another embodiment of a tampon device, the distal porous foam cup has a rim which encircles the cervix. The rim has high concentrations of medication and is positioned away from the direct flow of blood which exudes from the cervix during menstruation.

In another embodiment of a tampon device, the distal porous foam cup has a rim which encircles the cervix. The rim has fingers extending into the fornix areas around the cervix and the tips of the fingers have high concentrations of medication and are positioned away from the direct flow of menstrual blood.

In another embodiment of a tampon device, a distal porous foam section is in the shape of a scoop, which only partially encircles the cervix. The porous foam scoop has a nib-like shape which is designed to wedge itself into the posterior fornix. The porous foam scoop is designed to deliver medication to the vaginal wall along the entire length of the porous foam scoop.

In another embodiment, a tampon device is sheathed in a thin, supple, non-porous material such as a plastic film or a coated gauze that surrounds the absorbent tampon material like a skirt and opens like an umbrella when it comes in contact with the vaginal environment. A band of drug, ideally suspended in a wax-like carrier that melts at body temperature, encircles the sheathed tampon. Contact with vaginal fluids or menstrual flow causes the tampon to swell, forcing the skirt to open like an umbrella and to press tightly against the vaginal wall, putting the drug in contact with the vaginal mucosa while effectively preventing the drug from being absorbed into the tampon.

In another embodiment of a tampon device, distal fibers of the tampon which contact the cervix have high concentrations of pharmaceutical agent for delivery of the agent to the cervical tissue.

In another embodiment of a tampon device, the tampon device has an outer tubing having perforations, the outer tubing is concentric around an axial tube. The device has a distal porous foam section which in its dehydrated state is tight around the outer tubing. A bladder is located proximally to the porous foam and filled with liquid pharmaceutical agent. The bladder is connected to the outer tubing. An outer sheath covers the tampon. The sheath has an annular constriction distal to the bladder such that deployment of the tampon through the distal end of the sheath causes the liquid in the bladder to be forced out distally through the perforated outer tubing and into the porous foam.

In another embodiment of a tampon device, the tampon device has an annular delivery composition around the distal end. The composition contacts the vaginal epithelium for delivery of the agent. A non-absorbing axial tube opens distally and extends into the tampon for conducting blood flow to the absorbent material proximal to the porous foam. The annular composition can be a suppository, foam, paste, or gel.

Embodiments of the invention may include tampon devices of a standard length, or may be longer than standard tampons to facilitate locating the tampon device closer to or in contact with the cervix.

Devices of the invention are illustrated in FIGS. 3–21.

FIG. 3 is a cross-sectional representation of a portion of the female reproductive organs, including the uterus and the vagina in the upright orientation, and FIG. 4 is a cross-sectional side view representation thereof. The uterus 2 is a muscular organ enclosing the womb 4, and opening at the cervix 5 via the cervical canal or cervical os 6. The vagina 8 is defined by a muscular tube 10 leading from the labia minora 12 and labia majora 14 to the cervix 5. The local vasculature associated with the walls of the vagina 8 communicate with the uterine muscle vascular and lymphatic systems (not illustrated).

FIG. 5 is a cross-sectional representation of FIG. 3 showing placement of a drug delivery system 16 in the vagina 8a position which introduces drugs intravaginal ly to the uterus 2 by way of the vaginal blood vascular and lymphatic systems. Physiologically, this concept has been documented and confirmed in animal experiments reported herein.

Referring now to FIGS. 6–14, there being depicted various embodiments of tampon-like devices which can be used to deliver drugs for treatment of dysmenorrhea according to the invention. If a tampon-like device is used, there are numerous methods by which a drug can be incorporated into the device. For example, the drug can be incorporated into a gel-like bioadhesive reservoir in the tip of the device or attached as a strip to the tampon. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

The tampon-like device can be constructed so as to improve drug delivery. For example, the tampon can be shaped to fit in the area of the posterior fornix and pubic symphysis and constructed so as to open up to have maximum surface area of contact for drug delivery. If the drug is in a reservoir on the surface of the device, the shape of the device should be such that it can maintain the reservoir towards a vaginal mucosal orientation for best predictable drug release characteristics.

The tampon device can also be constructed so as to have a variable absorption profile. For example, the drug area at the tip of the tampon device could be different from that of the more proximal area in order to force the drug to diffuse out into tissue, as opposed to down into the absorbent part of the tampon. Alternatively, there could be a non-absorbing channel around the cervix for the first centimeter or so in order to minimize menstrual flow from washing away the drug composition.

The release of drug from the tampon device should be timed to provide proper uterine concentration of the drug over a typical length of use of a tampon device, usually 1–8 hours.

FIG. 6 is a cross-sectional representation of the vaginal area, adjacent the cervix 5, with a first embodiment of a tampon drug delivery system according to the invention. The tampon device 22 comprises an absorbent cylindrical tampon 24 comprised of fibrous material, for example cotton, having around its distal end 26 an annular delivery composition 28. The tampon device 22 places the annular delivery composition 28, supported around the distal end 26 of the tampon device 22, against the upper epithelium 18 of the vagina 8 and posterior fornix 20 for delivery through the vaginal surfaces in which the annular composition 28 is in contact. The annular composition 28 can be an annular suppository, foam, paste, or gel composed of suitable delivery components. During menses, the uterine discharge is absorbed by the tampon 24 and is prevented from carrying away the treatment composition.

FIG. 7 is a cross-sectional representation of the vaginal area adjacent the cervix 5 with a second embodiment of a tampon drug delivery system according to the invention. In this embodiment, tampon device 32 includes a non-porous tube 34 which communicates with the cervical os 6 for delivery of the menstrual discharge from the cervical os to an absorbent cylindrical tampon 36 comprised of fibers, for example cotton, for absorbing the discharge. The tube 34 prevents contact of the discharge with an annular drug delivery composition 38.

FIG. 8 is a cross-sectional representation of the vaginal area adjacent the cervix 5 with a third embodiment of a tampon drug delivery system according to the invention. In FIG. 8, the tampon device 42 includes a distal porous foam section 43 which is in the shape of a cup in the expanded state. In the center of the porous foam section 43 is a non-porous tube 44 which will conduct blood flow to absorbent tampon 45 proximal to the porous foam section 43. The porous foam is preferably a soft, light weight, physiologically inert foam material of polyurethane, polyester, polyether, (e.g., as described in U.S. Pat. No. 4,309,997) or other material such as collagen (e.g., as described in U.S. Pat. No. 5,201,326). The axial tube is preferably a non-absorptive physiologically inert material, such as rubber or plastic, and can be coated on its inner surface with an anticoagulant. The proximal end 46 of the tube 44 has a plastic loop 47 to which a string 48 may be tied for removal of the tampon device 42. The cup-shaped porous foam section 43 fits around the cervix 5 of the uterus 2 and contains medication which may be delivered to the cervical tissue.

FIG. 9A is a cross-sectional representation of the vaginal area adjacent the cervix 5 with a fourth embodiment of a tampon drug delivery system according to the invention. In FIG. 9A, the tampon device 52 includes a distal porous foam cup 54 and a proximal absorbent tampon 56. The porous foam cup 54 has a rim 58 which encircles the cervix 5, and which contains high concentrations of medication. The rim 58 area of the porous foam cup 54 is away from the direct flow of blood. The tampon device 52 includes a string 59 for removal of the tampon device 52. FIG. 9B is a cross-sectional view of the embodiment shown in FIG. 9A, taken in the direction indicated by the arrows labeled 9B in FIG. 9A. As illustrated in FIG. 9B, the rim 58 area forms a ring which contains a high concentration of medication. Alternatively, as illustrated in FIG. 10, the entire porous foam cup 55 may contain medication, not just in the ringed tip area 59 near the cervix 5.

FIG. 11A is a cross-sectional representation of the vaginal area adjacent the cervix 5 with a fifth embodiment of a tampon drug delivery system according to the invention. In FIG. 10A, the tampon device 62 includes a proximal absorbent tampon 64 and a distal section 66 which includes a dissolvable suppository or gel capsule 67 filled with liquid medication. The medication prior to dissolution or release of the liquid has a "doughnut" shape to allow for blood to pass through the center of the tampon 64. The tampon device 62 includes a string 68 attached to the tampon 64 for removal of the tampon device 62. FIG. 11B is a cross-sectional view of the the of the embodiment shown in FIG. 11A, taken in the direction indicated by the arrows labeled 11B in FIG. 11A, and illustrates the doughnut shape of the medication filled suppository or gel capsule 67.

FIG. 12 is a cross-sectional representation of the vaginal area adjacent the cervix 5 with a sixth embodiment of a tampon drug delivery system according to the invention. In FIG. 12A, the tampon device 72 includes a porous foam distal section 74 which is in the shape of a cup with "fingers" 76 which extend into the fornix areas 20 around the cervix 5. The tips of the fingers 76 contain high concentrations of medication which may be delivered to areas away from the direct flow of blood as the blood moves into absorbent tampon 78 proximal to the cup-shaped porous foam distal section 74. The tampon device 72 includes a string 79 for removal of the tampon device 72. FIG. 12B is a side view of the porous foam cup 74 and illustrates the fingers 76 which extend into the fornix areas 20 around the cervix 5 (FIG. 12A).

It will be readily apparent to a person skilled in the art that the characterization of the drug delivery device as having an annular shape is only an approximate description of the shape formed by fluid or semisolid drug delivery devices positioned around a cylinder and in contact with adjacent vaginal wall epithelium, and all shapes which conform to the vaginal epithelium and external cervical surfaces are intended to be included within and indicated by the term "annular". Moreover, use of the term "annular" does not restrict the invention to the use of such devices which encircle the entire cervix (i.e. 360 degrees). Devices which span an angle of less than 360 degrees, but which make sufficient contact with the vaginal epithelium to deliver sufficient quantity of the drug are within the scope of the invention.

The annular drug delivery composition (FIGS. 6 or 7) can be an absorbent material which expands in the presence of fluid or body heat to completely fill the space between the tampon 22, 32 and the vaginal epithelium 18.

FIG. 13 illustrates such a drug delivery device having an annular shape which does not completely encircle the entire cervix. FIG. 13 is the representation of FIG. 4 showing placement of a seventh embodiment of a tampon device 80 incorporating a scoop-shaped porous foam section 85. FIG. 14 is a side view of the tampon device 80 and FIG. 15 is a front view of the tampon device 80. The scoop-shaped porous foam section 85 is annular in shape, but does not completely encircle the cervix 5. Instead, the scoop-shaped porous foam section has a nib-shaped tip 81 which is designed to wedge itself into the posterior fornix 20. The scoop-shaped porous foam section 85 is designed to deliver medication to the vaginal wall along the entire length of the scoop-shaped porous foam section 85.

FIG. 16 is a cross-sectional representation of the vaginal area adjacent the cervix 5 with an eighth embodiment of a tampon drug delivery system according to the invention. In FIG. 15, the tampon device 82 comprises an absorbent tampon 84. The section 86 of the tampon 84 which rests against the cervix 5 contains high concentrations of medication. As the fibers absorb fluid, the tampon 84 expands around the cervix 5 and delivers medication to the tissue. The blood will be drawn to proximal sections of the tampon 84 as fibers become more absorbent in this area. The tampon device 82 includes a string 88 for removal of the tampon device 82.

Suitable cylindrical cartridge containers or inserter tubes which assist in the insertion and storage of the tampon systems of the present invention will be apparent to those skilled in the art of tampon construction. Examples are described in U.S. Pat. Nos. 4,3178,447; 3,884,233; and 3,902,493.

In general practice, a drug delivery tampon device as described herein is placed into the vagina and the inserter tube is removed. The tampon device contacts the inner wall of the vagina and the penetration enhancer and mucoadhesive act to facilitate the adsorption of the drug into the local vasculature. This results in a higher concentration of the drug being delivered to the systemic circulation.

Figure 17:
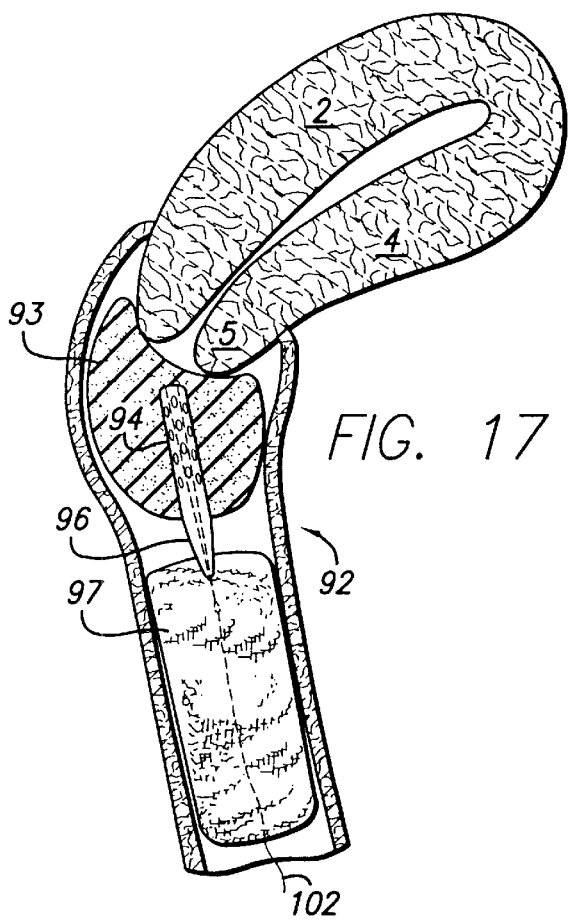
FIG. 17 is the representation of FIG. 4 showing placement of a tampon for drug delivery incorporating non-absorbent tubing comprising a distal opening.
Figure 18:
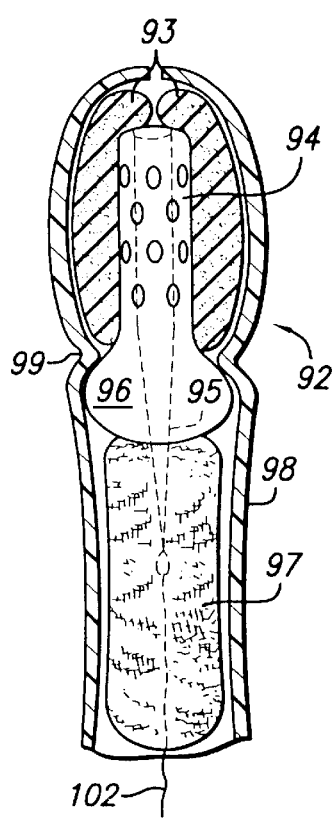
FIG. 18 is the tampon drug delivery system of FIG. 17 in a dehydrated, sheathed, state.
Figure 19:
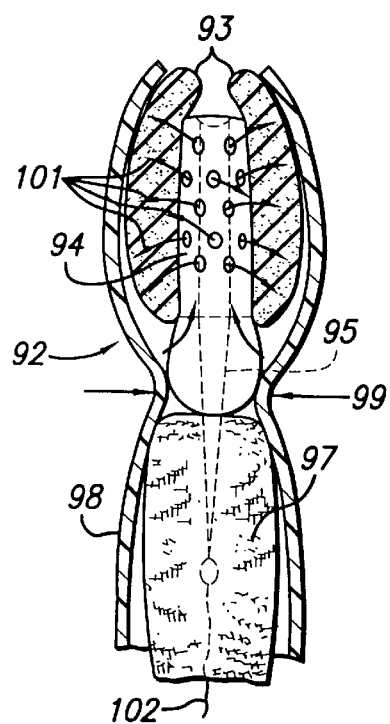
FIG. 19 is the tampon drug delivery system of FIG. 18 illustrating deployment of the tampon.

FIG. 17 is a cross-sectional representation of the vaginal area adjacent the cervix 5 with a ninth embodiment of a tampon drug delivery system according to the invention. In FIG. 17, the tampon device 92 includes a distal porous foam section 93 which, in its dehydrated, sheathed state (FIG. 18), is tight around a perforated outer tube 94. The perforated outer tube 94 is connected to a bladder 96 located proximally which is filled with liquid medication (not illustrated). Within the perforated outer tube 94 is a concentric inner tube 95 which provides a pathway for blood to flow into an absorbent tampon 97 which is proximal to the porous foam section 93. Prior to insertion, the tampon device 92 is enveloped in a sheath 98 which is necked down 99 between the porous foam section 93 and the bladder 96 50 that, when the tampon device 92 is deployed and the sheath 98 moves over the bladder 96, the medication is forced out 101 through the perforated outer tube 94 into the porous foam section 93 (FIG. 19). The tampon device 92 includes a string 102 for removal of the tampon device 92.

Another example of a suitable controlled release drug delivery system for the present invention is the vaginal ring. Vaginal rings usually consist of an inert elastomer ring coated by another layer of elastomer containing the drug to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

Pessaries, tablets and suppositories are other examples of drug delivery systems which can be used in the present invention. These systems have been used for delivery of vaginal medications and steroids, and have been described extensively in the literature.

Another example of a delivery system is the vaginal sponge. The desired pharmaceutical agent can be incorporated into a silicone matrix which is coated onto a cylindrical drug-free polyurethane vaginal sponge, as described in the literature.

Bioadhesive tablets are another drug delivery system. These bioadhesive systems use hydroxy propyl cellulose and polyacrylic acid. They release drugs for up to five days once they are placed in the appropriate formulation.

III. Treatment of Osteoporosis Paget's Disease and Related Bone Skeletal Diseases A method for treatment of osteoporosis, Paget's disease, bone and skeletal disease is based on the concept that the upper vagina is amply supplied with blood vessels connected to general circulation to permit preferential delivery of biphophonates via the transvaginal delivery to the circulation. This permits the higher concentrations of bisphosphonates to be delivered into circulation and to the bones than can be accomplished by oral administration.

Additionally, the treatment for osteoporosis or other diseases, as discussed below, may further comprise administration of a composition which in addition to the bisphosphonate contains an estrogen, or in alternative the estrogen may be administered systemically in conjunction with the vaginal bisphosphonate treatment. In another alternative, the device may contain the exothermic portion or electrical stimulating device for release of the drug from the device.

This direct delivery of bisphosphonates results in much higher systemic bioavailability of the bisphosphonate without accompanying undesirable adverse reactions.

The concept of transvaginal delivery to the blood has been confirmed in the rabbit model utilizing several drugs. The rabbit is the classic model for studying transvaginal drug delivery and extrapolations to people have generally be applicable.

The most specific demonstration of the concept has been achieved with the drug alendronate, as described in Example 4. Studies described in Example 4 demonstrate preferential binding of the formulated drug to the vagina for transvaginal delivery as compared to intravenous administration.

I. Treatment of Osteoporosis

The major effect of currently available antiresorptive therapy for osteoporosis is to slow or arrest bone loss. Although antiresorptive therapies demonstrate increases in bone mineral density, the effect is usually transient, and a plateau in bone mineral density usually emerges at one year. When the treatment with the alendronate is continued, a steady improvement in bone mineral density occurs in years 2 and 3.

II. Treatment of Postmenopausal Osteoporosis

Osteoporosis is a disorder of skeletal fragility characterized by an imbalance in bone turnover such that bone resorption exceeds bone formation. Accelerated bone resorption is the principal physiological derangement responsible for both postmenopausal and age-related bone loss. Furthermore, increased bone turnover is itself a risk factor for fracture, independent of bone mineral density. Recent studies with etidronate, pamidronate, and alendronate demonstrate the ability of these drugs to suppress bone turnover and to preserve or increase bone mass. Both in large studies with alendronate and in long-term studies with clodronate in patients at high fracture risk treated with etidronate, decreased fracture occurrence was observed. Except for upper gastrointestinal intolerance with aminobisphosphonates, these drugs are very well tolerated. Bisphosphonates are promising alternative to estrogen for the treatment of patients with decreased bone mass and, particularly, those with severe osteoporosis.

C. Treatment of Paget's Disease

Paget's disease of bone is a localized, monostotic or polyostotic disease characterized by increased bone remodeling, bone hypertrophy, and abnormal bone structure that in symptomatic patients leads to pain and bone deformity. Complications involve the bone fractures, neoplastic degeneration, or osteoarthritis of joints. The short-term objective of treatment is to alleviate bone pain, and the long-term objective is to minimize or prevent the progression of the disease.

Bisphosphonates, such as alendronate and pamidronate are used, in patients successfully treated with bisphosphonates, the new bone forms during treatment which bone appears to be lamellar rather than woven in structure. This histologic change is accompanied by major clinical, biochemical, and radiographic signs of improvement in the patient. With new bisphosphonate drugs, the suppression of disease activity is now attainable.

D. Metastases From Breast Cancer

Clinical research over the last decade has confirmed the helpful role of bisphosphonates in the management of patients with bone metastases secondary to breast cancer and other malignancies. This role is also expanding in myeloma and in the management of osteoporosis. Current clinical research in oncology is focusing on their potential for the prevention of skeletal complications of malignant disease and the development of bone metastases while basic researchers are developing compounds of higher potency and, perhaps, higher therapeutic efficacy.

One of the earliest bisphosphonates investigated, etidronate, who found effective in the management of malignant hypercalcemia and, when used orally and intermittently, its administration results in reduced bone loss in osteoporosis.

Clodronate has been shown to be an effective agent in the management of hypercalcemia and can be used as a single intravenous administration for this purpose. Clodronate is also effective in some patients in reducing bone pain and improving mobility. When used orally, it can, as can pamidronate, reduce the skeletal complications of breast cancer such as hypercalcemia, bone fractures and bone pain. It may have fewer gastrointestinal side effects than oral pamidronate. There is emerging evidence that bisphosphonates may delay or prevent the clinical appearance of bone metastases as well as reduce other skeletal complications.

E. General Method for Transvaginal Treatment

In general, the method of the invention comprises intravaginal insertion of a device comprising a bisphosphonate selected from the group consisting of alendronate, risedronate, clodronate, pamidronate, etidronate, tiludronate, neridronate and ibandronate for treatment of osteoporosis in a pharmaceutically acceptable, non-toxic carrier combined with a suitable delivery device or system which permits the transvaginal delivery of the drug to the blood circulation and bones through the vaginal mucosa.

The systems and methods of the invention provide several advantages over oral administration of drugs.

First, there is an increased concentration of drug delivered to the circulation due to bypassing gastrointestinal tract delivery. This provides for higher blood bioavailability of the drug by transvaginal delivery when compared to oral or intravenous administration, as described above.

Second, there is reduction of metabolism in the liver by avoiding the gastrointestinal system.

Third, the invention provides a continuous drug depot which allows continuous and uninterrupted delivery of drug over a long period of time.

Fourth, and very important, is the reduction of side effects, particularly irritation and inflamation of esophagus and stomach mucosa. For example, the well established gastrointestinal side-effects of observed with oral administration of bisphosphonates do not arise with transvaginal administration, in the same way as with oral administration, as described herein.

Other features of the invention will become apparent in the course of the following descriptions of exemplary embodiments which are given for illustration of the invention and are not intended to be limiting thereof.

UTILITY

The present oral route for administering the bisphosphonates provides inadequate bioavailability of the active pharmaceutical agent and/or results in unacceptable side effects of gastrointestinal toxicity. The inhibition of their absorption by food makes dosing extremely inconvenient.

The method of transvaginal delivery and the compositions described herein, when applied to the vaginal epithelium, are sufficient to deliver a therapeutically effective dose of the bisphosphonates.

EXAMPLE 1

Preparation of Alendronate Vaginal Suppository

This example describes a process for preparation of intravaginal suppositories.

The dose of alendronate (Sigma/Aldrich, St. Louis, Mo.) was 0.14 mg/kg body weight. Radioactively labeled alendronate (4–7 $\mu$Ci) $^3$H was added to the unlabeled compound.

Vaginal suppositories were formulated and prepared 24 hours prior to each experiment. The three basic ingredients for the suppositories were SUPPOCIRE® AS2 (Gattefosse, Westwood, N.J.) (75% wt); hydroxypropyl methylcellulose (HPMC) (obtained as METHOCEL® K, HPMC K15M, from Dow Chemical, Midland, Mich. (10% wt), a mucoadhesive agent; and TRANSCUTOL® (Gattefosse) (15% wt) a penetration enhancer.

To make eight suppositories, 4.5 grams of SUPPOCIRE, 600 mg of HPMC, 900 mg of TRANSCUTOL, the calculated dose of the drug, and its labeled counterpart were weighed out. SUPPOCIRE was melted in a disposable 100 mL polypropylene beaker suspended in water at 50° C. The solution was stirred until completely melted. HPMC and TRANSCUTOL were then added and mixed. Finally, the unlabeled drug and the radioactively-labeled drug were added to the warm solution. The warm mixture was quickly poured into TYGON® tubing molds available from Fisher Scientific, Pittsburgh, Pa. (2 cm lengths). The tubing was kept upright on an ice-cold glass slab. Suppositories were kept refrigerated until use. The suppository was weighed prior to each experiment to determine and confirm the actual drug dose.

EXAMPLE 2

Preparation of Pamidronate Vaginal Suppository

This example describes preparation of pamidronate containing suppositories.

$^{14}$C-Pamidronate is commercially obtained from Amersham Life Science, Arlington Hts., Ill. The dose of unlabeled pamidronate (Sigma/Aldrich) was 0.2 mg/kg body weight.

All the other steps in the preparation of the pamidronate suppositories are identical to those of Example 1 with pamidronate replacing alendronate.

Suppositories comprising other bisphosphonates are prepared in the same way except that their amount may vary.

EXAMPLE 3

Alendronate Pharmacokinetic Studies

This example describes procedures used for pharmacokinetic studies for alendronate intravaginal and transvaginal delivery.

$^3$H-Alendronate was obtained from DuPont/NEN, Boston, Mass. Prior to intravenous injection, unlabeled alendronate (Sigma/Aldrich, St. Louis, Mo.) (0.15–0.6 mg/kg body weight, i.v.) was dissolved in 0.5 mL dimethyl sulfoxide (Syntex, West Des Moines, Iowa). Labeled alendronate (4–7 $\mu$Ci) was then added to the cold compound just prior to i.v. injection.

Female white New Zealand rabbits weighing 2.8 to 3.5 kg were obtained from Myrtle Rabbitry (Thompson Station, Tenn.). Rabbits were kept in a National Institutes of Health approved facility and were acclimated to their environment at least 48 hours prior to each experiment.

Drug pharmacokinetic studies were performed via both the intravenous, oral and transvaginal modes of administration. During the first series of experiments, the intravenous route of administration was utilized to determine the initial half-lives of the experimental compound. In the second series of experiments, the intravenous and transvaginal routes of administration were compared in the same rabbit.

For the half-life experiments, after an 18 hour overnight fast, each rabbit was premedicated with ketamine (35 mg/kg, i.m.), xylazine (5 mg/kg, i.m.), and atropine (0.5 mg, i.m.). Each rabbit was intubated and anesthesia was maintained with isoflurane (1–3%). Vital signs were monitored throughout the experiment via a pulse oximeter. Rabbit body temperature was kept constant by a recirculating heating pad. Intravenous access was achieved by placement of a 22 gauge TEFLON catheter in the peripheral ear vein. Intra-arterial access was achieved by placement of a 22 gauge TEFLON catheter in the central artery in the ear. A heat lamp was used to warm the ears to promote peripheral blood flow.

After the rabbit was anesthetized, the mixture containing labeled and unlabeled drug was injected through the ear vein over a 10 second to 2 minute period. Blood samples were drawn through the arterial line at 0.1, 0.25, 0.5, 0.75, 2, 4, 6, 8, 10, 12 and 24 hours relative to the time of injection. Blood samples (1 mL) were placed in a polypropylene tube containing EDTA. The blood was centrifuged at 2000 rpm for 10 minutes and 0.5 mL of plasma was placed into a scintillation vial.

Solvable tissue solubilizer 0.5 mL (Packard, Meridian, Conn.) was added to the plasma samples and samples were vortexed for 30 seconds. 10 mL of Hionic-Fluor scintillation cocktail (Packard) was added and samples were vortexed for 1 minute before they were placed on the scintillation counter.

For the transvaginal experiments, vaginal suppositories were formulated and kept on ice. The suppository was introduced into the rabbit vagina using the barrel of a plastic transfer pipette (Baxter, McGaw Park, Ill.) and a tuberculin syringe as the plunger to load the suppository into the vagina to a depth of 7 to 8 cm. Blood samples were taken at 0.1, 0.25, 0.5, 0.75, 2, 4, 6, 8, 14, 20 and 25 hours relative to suppository administration.

The rabbit was allowed to recover and a 7-day washout period was carried out prior to the vaginal administration.

Alendronate was administered as described above and also orally. As shown in Table 1 above, plasma levels of alendronate administered intra and transvaginally were fifteen times as high as those observed after oral administration and persisted for a prolonged period of time.

EXAMPLE 4

Preparation of a Gel Containing Alendronate for Intravaginal Application

This example describes the process for preparation of gel composition.

250 mL of isotonic saline was heated to 80° C. and 1.50 grams of METHOCEL are added, with stirring. The resultant mixture was allowed to stand at room temperature for 2 hours. Then 120 mg of alendronate mixed together with 10 mg of Tween 80. The alendronate/Tween mixture and a quantity of isotonic saline sufficient to bring the total volume to 500 mL were added to the gel and thoroughly mixed.

The gel was incorporated into the intravaginal tampon.

EXAMPLE 5

Preparation of Pamidronate Containing Lotion for Intravaginal Application

This example describes the preparation of pamidronate containing lotion.

Pamidronate (50 mg) is added to one mL of JERGENS® standard fragrance free lotion. The mixture is stirred until pamidronate is equally distributed within the lotion.

EXAMPLE 6

Preparation of Clodronate Containing Gel for Intravaginal Application

This example describes the preparation of clodronate containing compositions.

Clodronate (Sigma/Aldrich, St. Louis, Mo.) (200 mg) is added to one mL of gel comprised of the following ingredients: glycerin, mineral oil, polycarbophil, carbomer 934P, hydrogenated palm oil, glyceride, sodium hydroxide, sorbic acid, and purified water.

Resulting composition was incorporated into a tampon-like device by soaking the device in the composition.

EXAMPLE 7

Preparation of Bisphosphonate Containing Vaginal Suppositories

This example describes the preparation of bisphosphonate containing vaginal suppositories for use in human patients.

A vaginal suppository is prepared for human intravaginal administration of each one of the drugs alendronate, risedronate, clodronate, etidronate, pamidronate, tiludronate and neridronate at the indicated dose. All of the steps in the preparation of the drug suppository are identical to those of Example 1 except that no radiolabeled compound is used and the therapeutical amount of the drug is used.

The quantity of vaginal dosage form needed to deliver the desired dose will of course depend on the concentration of the active ingredient in the composition. The therapeutic dosage range for vaginal administration of the compositions of the present invention will vary with the size of the patient and the degree of the affliction.

EXAMPLE 8

Preparation of Vaginal Medicated Tampons

This example describes the preparation of a medicated device of the invention.

Preparation of vaginal medicated tampons is essentially as described in Example 7. The drugs listed in Example 7 are added to the tampon materials as gels, creams, ointment, powders, solutions, suspension, emulsions or suppository either before the tampon is fabricated or the prefabricated tampons are soaked in the solution, suspension, emulsion or other fluid preparation. The amount of the drug is such that it assures that the dose administered by vaginal tampon is at least as high as the one indicated in Example 8 and is delivered transvaginally in a dose linear manner, as much as possible.

EXAMPLE 9

Vaginal Ointment

Vaginal ointment according to the invention comprises an oil and an aqueous phase.

| Oil Phase | Aqueous Phase |
| --- | --- |
| Acetylated lanolin | Water |
| Mineral oil 70 | Bisphosphonate |
| Amerchol L-500 | Preservative |
| Amerchol CAB | Mucoadhesive |
| Microcrystalline wax | |
| Cetyl alcohol | |
| Brij 52 | |
| Brij 58 | |

For preparation of the ointment the drug selected from the group of compounds consisting of alendronate, clodronate tiludronate, pamidronate, etidronate, ibandronate, neridronate, residronate, zoledronate or olpadronate is dissolved in the aqueous phase and the oil phase added. Both phases are properly mixed.

EXAMPLE 10

Vaginal Cream

Vaginal cream comprises phase A components and phase B components.

| Phase A | Phase B |
| --- | --- |
| Purified water | Light mineral oil |
| Borax | Synthetic beeswax |
| Methylparabe | Glyceryl monostearate, pure |
| Bisphosphonate | Propylparaben |

Methylparaben, borax and the bisphosphonate is dissolved in water. Propylparaben is dissolved in as well mixed mixture pf phase B. Phase B is added to phase A with rapid stirring.

EXAMPLE 11

Vaginal Powder

Vaginal powder is prepared by dissolving hydroxypropyl cellulose in water with heat. The mixture is slightly cooled and the bisphosphonate is added. The mixture is lyophilized.

EXAMPLE 12

Vaginal Tablet

Tablet for vaginal delivery is manufactured either by wet granulation or direct compression.

The following components are used:

Microcrystalline cellulose

Anhydrous lactose

Crosscarmellose sodium

Magnesium stearate

Bisphosphonate

EXAMPLE 13

Vaginal Capsule

Vaginal capsule is prepared by filling the powder prepared according to Example 11 into capsules.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A method for a transmucosal delivery of bisphosphonates to a systemic circulation for treatment and prevention of osteoporosis and Paget's disease and for treatment of a metastatic bone disease in a human female patient, wherein a bisphosphonate is delivered into the systemic circulation through a vaginal mucosa from a vaginal device incorporated with a transmucosal vaginal composition, said method comprising steps of:
   a) providing the transmucosal vaginal composition consisting essentially of from about 0.001 to about 2000 mg of the bisphosphonate selected from the group consisting of alendronate, clodronate, etidronate, pamidronate, tiludronate, ibandronate, neridronate, risedronate, zoledronate and olpadronate;
      from about 40 to about 95% of a saturated mono-, di- or triglyceride of fatty acids from 8 to 18 carbons or a mixture thereof;
      from about 5 to about 25% of a mucoadhesive agent selected from the group consisting of alginate, pectin and a cellulose derivative; and
      from about 5 to about 25% of ethoxydiglycol;
      wherein said composition is formulated and incorporated into the device as a suppository, cream, gel, foam, ointment, capsule containing microparticles, microparticles or microcapsules;
   b) incorporating said composition into said vaginal device wherein said vaginal device is a vaginal tampon, vaginal ring, vaginal strip, vaginal capsule, vaginal tablet, vaginal pessary, vaginal cup or vaginal sponge; and
   c) delivering said composition to the vaginal mucosa by inserting said device into the vagina.

2. The method of claim 1 wherein said composition contains from about 1 to about 40 mg of alendronate, from about 100 to about 1600 mg of clodronate, from about 7.5 to about 750 mg of etidronate, from about 1 to about 20 mg of pamidronate, from about 2 to about 400 mg of tiludronate, from about 0.5 to about 50 mg of ibandronate, from about 0.01 to about 0.7 mg of neridronate, or from about 1 to about 80 mg of risedronate, from about 60 to about 85% of the saturated triglyceride of fatty acids, from about 5 to about 10% of the mucoadhesive agent and from about 10 to about 20% of ethoxydiglycol.

3. The method of claim 2 wherein said mucoadhesive agent is hydroxypropyl methylcellulose.

4. The method of claim 3 wherein said composition is consisting essentially of about 10% of hydroxypropyl methylcellulose, about 75% of saturated triglyceride of fatty acids and about 15% of ethoxydiglycol.

5. The method of claim 4 wherein the bisphosphonate is released from said composition incorporated into said device in a controlled release manner.

6. A method for treatment and prevention of osteoporosis and Paget's disease and for treatment of a metastatic bone disease in a human female patient by a transmucosal delivery of bisphosphonates to a systemic circulation wherein a bisphosphonate is delivered to, absorbed through and delivered into the systemic circulation through a vaginal mucosa from a transmucosal composition, said method comprising steps of:
   a) providing the transmucosal vaginal composition containing from about 0.001 to about 2000 mg of the bisphosphonate selected from the group consisting of alendronate, clodronate, etidronate, pamidronate, tiludronate, ibandronate, neridronate, risedronate, zoledronate and olpadronate;
      from about 40 to about 95% of a saturated mono-, di- or triglyceride of fatty acids from 8 to 18 carbons or a mixture thereof;
      from about 5 to about 25% of a mucoadhesive agent selected from the group consisting of alginate, pectin and a cellulose derivative; and
      from about 5 to about 25% of ethoxydiglycol;
      wherein said composition is formulated as a suppository, cream, gel, foam, ointment, capsule, capsule containing microparticles, microparticles or microcapsules; and
   b) delivering said composition to the vaginal mucosa.

7. The method of claim 6 wherein said composition contains from about 1 to about 40 mg of alendronate, from about 100 to about 1600 mg of clodronate, from about 7.5 to about 750 mg of etidronate, from about 1 to about 20 mg of pamidronate, from about 2 to about 400 mg of tiludronate, from about 0.5 to about 50 mg of ibandronate, from about 0.01 to about 0.7 mg of neridronate, or from about 1 to about 80 mg of risedronate, from about 60 to about 85% of the mon-, di- or triglyceride of fatty acids, from about 5 to about 10% of the mucoadhesive agent and from about 10 to about 20% of ethoxydiglycol.

8. The method of claim 7 wherein said mucoadhesive agent is a hydroxypropyl methylcellulose.

9. The method of claim 8 wherein said composition is consisting essentially of about 10% of hydroxypropyl methylcellulose, about 75% of the triglyceride of the saturated fatty acids and about 15% of ethoxydiglycol.

10. The method of claim 9 wherein said composition further comprises from about 5 to about 25% of solubilizing agent.

11. The method of claim 10 wherein the composition is administered daily, bi-daily, weekly, monthly or quarterly.

12. The method of claim 11 wherein said composition is administered once or twice daily.

13. The method of claim 12 wherein said composition is incorporated into a vaginal tampon and delivered by releasing said composition from said tampon in a controlled release manner.

14. A pharmaceutically acceptable transmucosal composition for transvaginal delivery of bisphosphonates to a human female patient, said composition consisting essentially of:

a bisphosphonate selected from the group consisting of
about 1 to about 40 mg/day of alendronate, about 100 to about 1600 mg/day of clodronate, about 7.5 to about 750 mg/day of etidronate, about 1 to about 20 mg/day of pamidronate, about 2 to about 400 mg/day of tiludronate, about 0.5 to about 50 mg/day of ibandronate, about 0.01 to about 0.7 mg/day of neridronate, and about 1 to about 80 mg/day of risedronate, formulated in admixture with about 10% of hydroxypropyl methylcellulose, about 75% of saturated mono-, di- or triglyceride of fatty acids, and about 15% of ethoxydiglycol wherein said composition is formulated and incorporated into a suppository, cream, gel, foam, ointment, capsule containing microparticles, microparticles, or microcapsules and wherein the composition is incorporated into a vaginal device wherein said vaginal device is a vaginal tampon, vaginal ring, vaginal strip, vaginal capsule, vaginal tablet, vaginal pessary, vaginal cup or vaginal sponge.

15. The composition of claim 14 wherein said bisphosphonate is alendronate formulated in a range of doses from about 1 mg to about 40 mg for administration as a daily, weekly or monthly dose.

16. The composition of claim 14 wherein said bisphosphonate is pamidronate formulated in a range of doses from about 1 mg to about 20 mg for administration as a daily, weekly or monthly dose.

17. The composition of claim 14 wherein said bisphosphonate is clodronate formulated in a range of doses from about 100 to about 1600 mg for administration as a daily, weekly or monthly dose.

18. The composition of claim 14 wherein said bisphosphonate is etidronate formulated in a range of doses from about 7.5 mg to about 750 mg for administration as a daily, weekly dose or monthly dose.

19. The composition or claim 14 wherein said bisphosphonate is tiludronate formulated in a range of doses from about 2 mg to about 400 for administration as a daily, weekly or monthly dose.

20. The composition of claim 14 wherein said bisphosphonate is neridronate formulated in a range of doses from about 0.01 mg to about 0.7 mg for administration as a daily, weekly or monthly dose.

21. The composition of claim 14 wherein said bisphosphonate is risedronate formulated in a range of doses from about 1 mg to about 80 mg for administration au a daily, weekly dose or monthly dose.

22. The composition of claim 14 wherein said bisphosphonate is ibandronate formulated in a range of doses from about 0.5 mg to about 50 mg for administration as a daily, weekly or monthly dose.

23. The composition of claim 14 additionally comprising an excipient selected from the group consisting of glycerin, polyoxyethylene sorbitan monooleate, mineral oil, polycarbophil, carbomer, hydrogenated palm oil, glyceride, sodium hydroxide and sorbic acids.

24. A medicated intravaginal device for a transmucosal delivery of bisphosphonates to the general circulation, wherein said device is a vaginal tampon, vaginal ring, vaginal strip, vaginal capsule, vaginal tablet, vaginal bioadhesive tablet, vaginal pessary, vaginal cup or vaginal sponge incorporated with a transmucosal composition consisting essentially of a bisphosphonate selected from the group consisting of 1 to about 40 mg/day of alendronate, about 100 to about 1600 mg/day of clodronate, about 7.5 to about 750 mg/day of etidronate, about 1 to about 20 mg/day of pamidronate, about 2 to about 400 mg/day of tiludronate, about 0.5 to about 50 mg/day of ibandronate, about 0.01 to about 0.7 mg/day of neridronate, and about 1 to about 80 mg/day of risedronate;

about 10% of hydroxypropyl methylcellulose;

about 75% of saturated triglyceride of fatty acids; and about 15% of ethoxydiglycol.

25. The device of claim 24 wherein said composition incorporated into said device is formulated as a suppository, cream, lotion, ointment, foam, capsule, capsule containing microparticles, microparticles, ointment, or gel.

26. The device of claim 25 suitable for transmucosal delivery of the bisphosphonate for treatment and prevention of osteoporosis and Paget's disease or for treatment of a metastatic bone disease in a human female patient wherein said device is configured to make and maintain a contact with a vaginal mucosa or epithelium.

27. The device of claim 26 wherein said device is the vaginal tampon impregnated with the transmucosal composition containing at least one bisphosphonate.

* * * * *